（12）United States Patent
Errico et al.

(10) Patent No.: US 11,065,444 B2
(45) Date of Patent: Jul. 20, 2021

(54) MOBILE PHONE FOR STIMULATING THE TRIGEMINAL NERVE TO TREAT DISORDERS

(71) Applicant: ElectroCore, Inc., Basking Ridge, NJ (US)

(72) Inventors: Joseph P. Errico, Warren, NJ (US); Steven Mendez, Chester, NJ (US); Bruce J. Simon, Mountain Lakes, NJ (US)

(73) Assignee: ElectroCore, Inc., Basking Ridge, NJ (US)

( * ) Notice: Subject to any disclaimer, the term of this patent is extended or adjusted under 35 U.S.C. 154(b) by 48 days.

(21) Appl. No.: 16/535,205

(22) Filed: Aug. 8, 2019

(65) Prior Publication Data
US 2019/0358451 A1 Nov. 28, 2019

Related U.S. Application Data

(60) Division of application No. 14/337,059, filed on Jul. 21, 2014, now Pat. No. 10,376,695, which is a
(Continued)

(51) Int. Cl.
*A61N 1/36* (2006.01)
*H04M 1/21* (2006.01)
(Continued)

(52) U.S. Cl.
CPC ....... *A61N 1/36021* (2013.01); *A61N 1/0456* (2013.01); *A61N 1/3603* (2017.08);
(Continued)

(58) Field of Classification Search
CPC .............. A61N 1/36021; A61N 1/3603; A61N 1/36034; A61N 1/37217; A61N 1/3756;
(Continued)

(56) References Cited

U.S. PATENT DOCUMENTS 3,590,810 A 7/1971 Kopecky
4,196,737 A 4/1980 Bevilacqua
(Continued)

FOREIGN PATENT DOCUMENTS

EP 1967226 9/2008
EP 2777764 8/2015
(Continued)

OTHER PUBLICATIONS

Greicius et al., Functional connectivity in the resting brain: A network analysis of the default mode hypothesis, PNAS, Jan. 2003, vol. 100, No. 1, pp. 253-258.
(Continued)

*Primary Examiner* — Amanda K Hulbert
*Assistant Examiner* — Natasha Patel
(74) *Attorney, Agent, or Firm* — Farber LLC

(57) ABSTRACT

Devices and methods are disclosed that allow a patient to self-treat a medical condition, such as migraine headache and trigeminal neuralgia and the like, by noninvasive electrical stimulation of nerves of the head, particularly supraorbital, supratrochlear, infraorbital, and mental nerves in the vicinity of their foramen or notch. The system comprises a handheld mobile device, such as a smartphone, that is applied to the surface of the patient's head. One or more electrodes on the mobile device apply electrical impulses transcutaneously through the patient's skin to the targeted nerve to treat the medical condition. The system is designed to address problems that arise particularly during self-treatment, when a medical professional is not present.

24 Claims, 12 Drawing Sheets

Related U.S. Application Data continuation-in-part of application No. 14/292,491, filed on May 30, 2014, now Pat. No. 9,375,571, and a continuation-in-part of application No. 13/858,114, filed on Apr. 8, 2013, now Pat. No. 9,248,286.

(60) Provisional application No. 62/001,004, filed on May 20, 2014, provisional application No. 61/752,895, filed on Jan. 15, 2013.

(51) Int. Cl.
| | |
|---|---|
| *A61N 1/04* | (2006.01) |
| *A61N 1/372* | (2006.01) |
| *A61N 1/375* | (2006.01) |
| *A61N 1/378* | (2006.01) |
| *A61B 5/00* | (2006.01) |
| *A61B 5/06* | (2006.01) |

(52) U.S. Cl.
CPC ..... *A61N 1/36025* (2013.01); *A61N 1/36034* (2017.08); *A61N 1/3756* (2013.01); *A61N 1/3787* (2013.01); *A61N 1/37217* (2013.01); *H04M 1/21* (2013.01); *A61B 5/0071* (2013.01); *A61B 5/066* (2013.01); *A61B 5/6898* (2013.01); *A61B 5/7425* (2013.01); *H04M 2250/12* (2013.01)

(58) Field of Classification Search
CPC ................ A61N 1/3787; A61N 1/0456; A61N 1/36025; H04M 1/21; H04M 2250/12; A61B 5/7425; A61B 5/066; A61B 5/0071; A61B 5/6898
See application file for complete search history.

(56) References Cited

U.S. PATENT DOCUMENTS

| | | | |
|---|---|---|---|
| 4,989,605 | A | 2/1991 | Rossen |
| 5,109,847 | A | 5/1992 | Liss et al. |
| 5,458,141 | A | 10/1995 | Neil |
| 5,487,759 | A | 1/1996 | Bastyr et al. |
| 5,782,874 | A | 7/1998 | Loos |
| 5,899,922 | A | 5/1999 | Loos |
| 5,983,131 | A | 11/1999 | Weaver et al. |
| 6,341,236 | B1 | 1/2002 | Osorio et al. |
| 6,463,327 | B1 | 10/2002 | Lurie et al. |
| 6,587,719 | B1 | 7/2003 | Barrett et al. |
| 6,610,713 | B2 | 8/2003 | Tracey |
| 6,631,297 | B1 | 10/2003 | Mo |
| 7,734,340 | B2 | 6/2010 | De Ridder |
| 7,797,041 | B2 | 9/2010 | Libbus et al. |
| 2002/0099417 | A1 | 7/2002 | Naritoku et al. |
| 2002/0183237 | A1 | 12/2002 | Puskas |
| 2002/0183804 | A1 | 12/2002 | Malaney et al. |
| 2003/0212311 | A1 | 11/2003 | Nova et al. |
| 2004/0073271 | A1 | 4/2004 | Harry et al. |
| 2004/0243182 | A1 | 12/2004 | Cohen et al. |
| 2004/0249416 | A1 | 12/2004 | Yun et al. |
| 2005/0021092 | A1 | 1/2005 | Yun et al. |
| 2005/0065574 | A1 | 3/2005 | Rezai |
| 2005/0113630 | A1 | 5/2005 | Fox et al. |
| 2005/0137644 | A1 | 6/2005 | Boveja et al. |
| 2005/0187590 | A1 | 8/2005 | Boveja et al. |
| 2005/0216062 | A1 | 9/2005 | Herbst |
| 2005/0267544 | A1 | 12/2005 | Lee et al. |
| 2006/0074284 | A1 | 4/2006 | Juola et al. |
| 2006/0074450 | A1 | 4/2006 | Boveja et al. |
| 2006/0100668 | A1 | 5/2006 | Ben-David et al. |
| 2006/0100671 | A1 | 5/2006 | Ridder |
| 2006/0173510 | A1 | 8/2006 | Besio et al. |
| 2006/0178703 | A1 | 8/2006 | Huston et al. |
| 2007/0027496 | A1* | 2/2007 | Parnis ................ A61N 1/3601 607/42 |
| 2007/0038264 | A1 | 2/2007 | Jaax et al. |
| 2007/0106337 | A1 | 5/2007 | Errico et al. |
| 2007/0123952 | A1 | 5/2007 | Strother et al. |
| 2007/0142886 | A1 | 6/2007 | Fischell et al. |
| 2007/0150006 | A1 | 6/2007 | Libbus et al. |
| 2007/0156182 | A1 | 7/2007 | Castel et al. |
| 2007/0173908 | A1* | 7/2007 | Begnaud ............ A61N 1/36025 607/63 |
| 2007/0276449 | A1 | 11/2007 | Gunter et al. |
| 2008/0021512 | A1 | 1/2008 | Knudson et al. |
| 2008/0027513 | A1 | 1/2008 | Carbunaru |
| 2008/0045776 | A1 | 2/2008 | Fischell et al. |
| 2008/0077192 | A1 | 3/2008 | Harry et al. |
| 2008/0114199 | A1 | 5/2008 | Riehl et al. |
| 2008/0132964 | A1 | 6/2008 | Cohen et al. |
| 2008/0177190 | A1 | 7/2008 | Libbus et al. |
| 2008/0208266 | A1 | 8/2008 | Lesser et al. |
| 2008/0306325 | A1 | 12/2008 | Burnett et al. |
| 2009/0112283 | A1 | 4/2009 | Kriksunov et al. |
| 2009/0132018 | A1 | 5/2009 | DiUbaldi et al. |
| 2009/0157149 | A1 | 6/2009 | Wahlgren et al. |
| 2009/0234417 | A1 | 9/2009 | Pastena et al. |
| 2009/0234419 | A1 | 9/2009 | Maschino et al. |
| 2009/0240297 | A1 | 9/2009 | Shavit et al. |
| 2009/0287035 | A1 | 11/2009 | Dietrich et al. |
| 2010/0030299 | A1 | 2/2010 | Covalin |
| 2010/0152794 | A1* | 6/2010 | Radivojevic ......... A61N 1/0452 607/2 |
| 2010/0286553 | A1 | 11/2010 | Feler et al. |
| 2011/0046432 | A1 | 2/2011 | Simon et al. |
| 2011/0152967 | A1 | 6/2011 | Simon et al. |
| 2011/0213295 | A1 | 9/2011 | Henley et al. |
| 2011/0218590 | A1* | 9/2011 | Degiorgio ............ A61N 1/0504 607/45 |
| 2011/0224749 | A1 | 9/2011 | Ben-David et al. |
| 2011/0230701 | A1* | 9/2011 | Simon ...................... A61N 1/40 600/9 |
| 2012/0029601 | A1 | 2/2012 | Simon et al. |
| 2012/0283697 | A1 | 11/2012 | Kim et al. |
| 2012/0303080 | A1 | 11/2012 | Ben-David et al. |
| 2013/0006322 | A1 | 1/2013 | Tai |
| 2013/0060304 | A1 | 3/2013 | LaTendresse et al. |
| 2013/0245486 | A1 | 9/2013 | Simon et al. |
| 2014/0005743 | A1 | 1/2014 | Giuffrida et al. |
| 2015/0165226 | A1 | 6/2015 | Simon et al. |
| 2015/0190637 | A1 | 7/2015 | Simon et al. |

FOREIGN PATENT DOCUMENTS

| | | |
|---|---|---|
| JP | 2009-125263 | 6/2009 |
| KR | 101242190 | 3/2013 |
| WO | WO1993/01862 | 2/1993 |
| WO | WO2005/007120 | 1/2005 |
| WO | WO2007/092062 | 8/2007 |
| WO | WO2008/042902 | 4/2008 |
| WO | WO2007/058780 | 5/2008 |
| WO | WO2009/021080 | 2/2009 |
| WO | WO2009/064641 | 5/2009 |
| WO | WO2009/135693 | 11/2009 |
| WO | WO2012/121750 | 9/2012 |
| WO | WO2013/066135 | 5/2013 |

OTHER PUBLICATIONS

Heneka et al., Locus ceruleus controls Alzheimer's disease pathology by modulating microglial functions through norepinephrine, PNAS, Mar. 2010, vol. 107, No. 13, pp. 6058-6063.

Lee et al., Clustering of Resting State Networks, PLoS One, Jul. 2012, vol. 7, Issue 7, pp. 1-12.

International Search Report and Written Opinion dated Aug. 25, 2015 in related Application No. PCT/US15/31847 filed May 20, 2015 (10 pages).

International Search Report and Written Opinion dated May 8, 2007 in related PCT Application No. PCT/US2006/042823 filed Nov. 2, 2006 (5 pages).

(56) References Cited

OTHER PUBLICATIONS

International Search Report and Written Opinion dated Sep. 17, 2007 in related PCT Application No. PCT/US2006/042828 filed Nov. 2, 2006 (5 pages).
International Search Report and Written Opinion dated Mar. 26, 2008 in related PCT Application No. PCT/US2006/042752 filed Nov. 1, 2006 (7 pages).
International Search Report and Written Opinion dated Dec. 22, 2011 in related PCT Application No. PCT/US2011/049844 filed Aug. 31, 2011 (9 pages).
KR101242190 dated Mar. 25, 2013, Espacenet computer generated English translation (11 pages).
International Search Report and Written Opinion dated Apr. 30, 2013 in related PCT Application No. PCT/US2013/023014 filed Jan. 24, 2013 (7 pages).
International Search Report and Written Opinion dated Dec. 11, 2013 in related PCT Application No. PCT/US2013/058079 filed Sep. 4, 2013 (8 pages).
International Search Report and Written Opinion dated Jan. 29, 2014 in related PCT Application No. PCT/US2013/068804 filed Nov. 6, 2013 (10 pages).
Europe Office Action dated Apr. 24, 2018 in related Application No. 15796247.3 filed May 20, 2015 (6 pages).
Europe Office Action dated Jul. 26, 2018 in related Application No. 11818591.7 filed Aug. 12, 2011 (8 pages).

\* cited by examiner

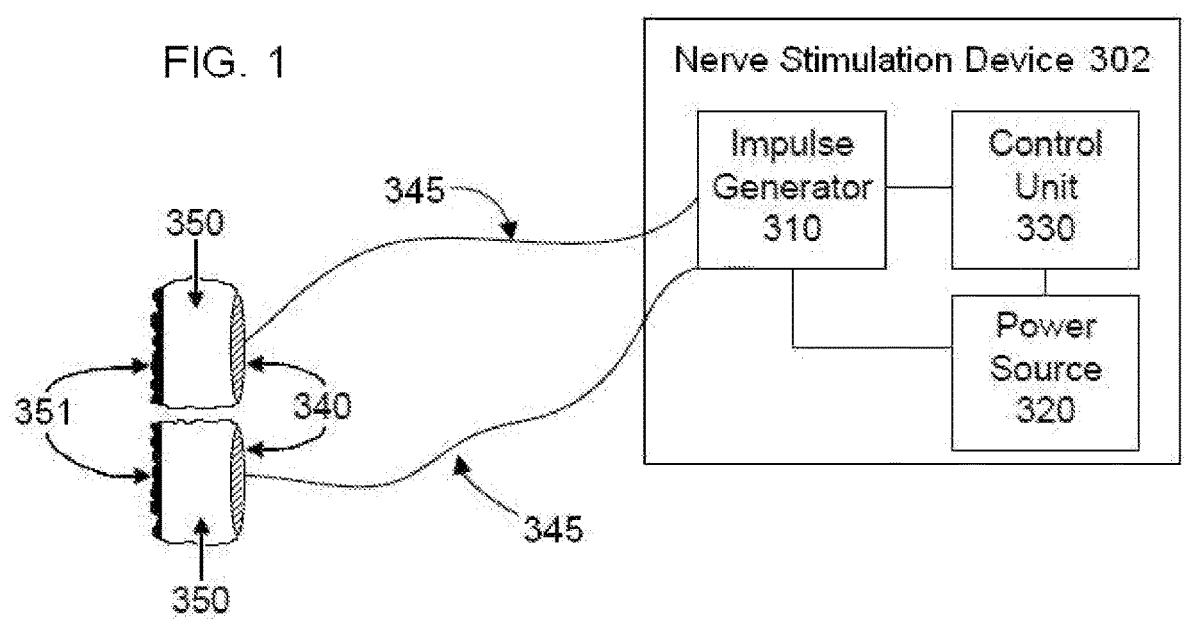

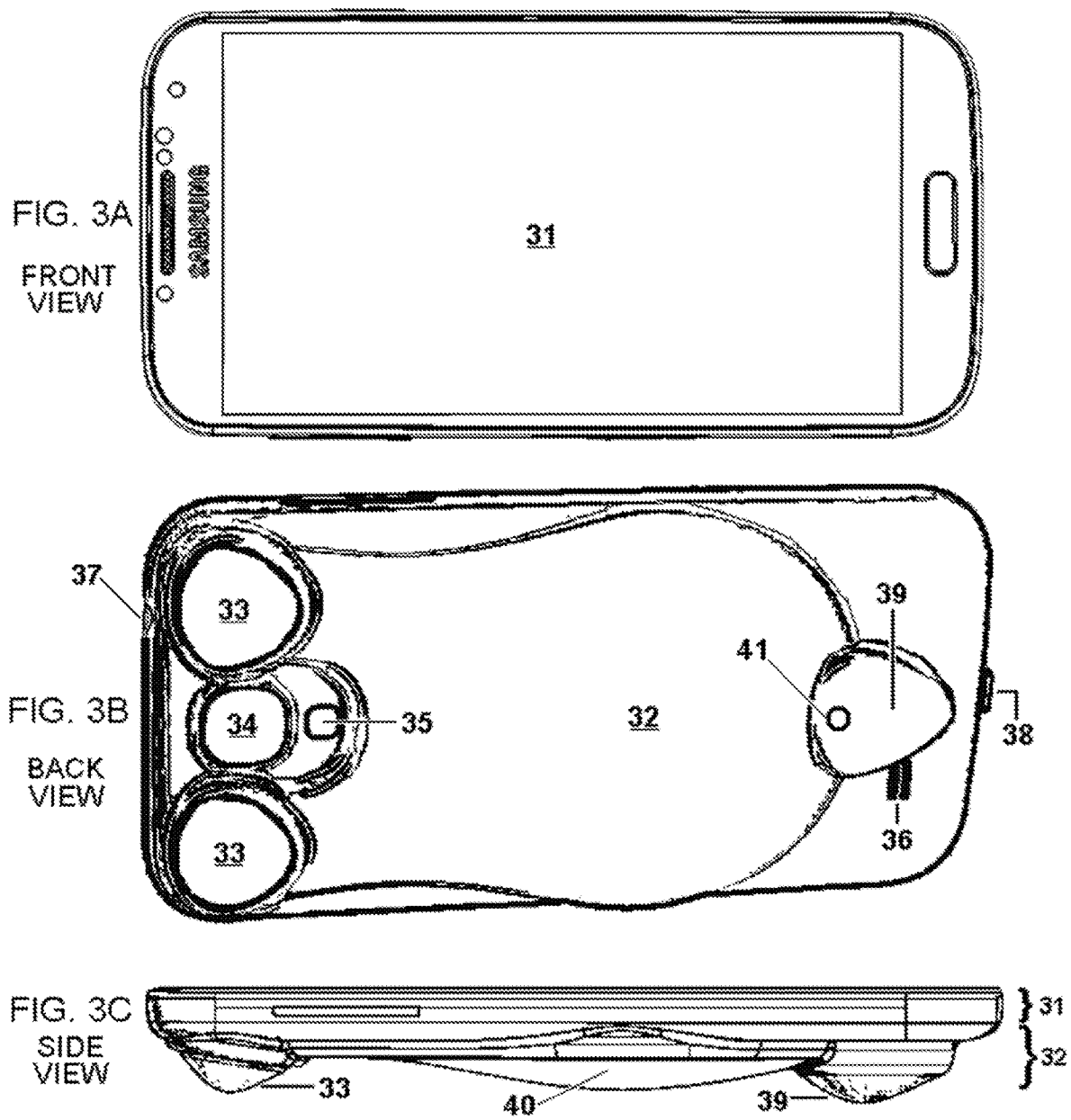

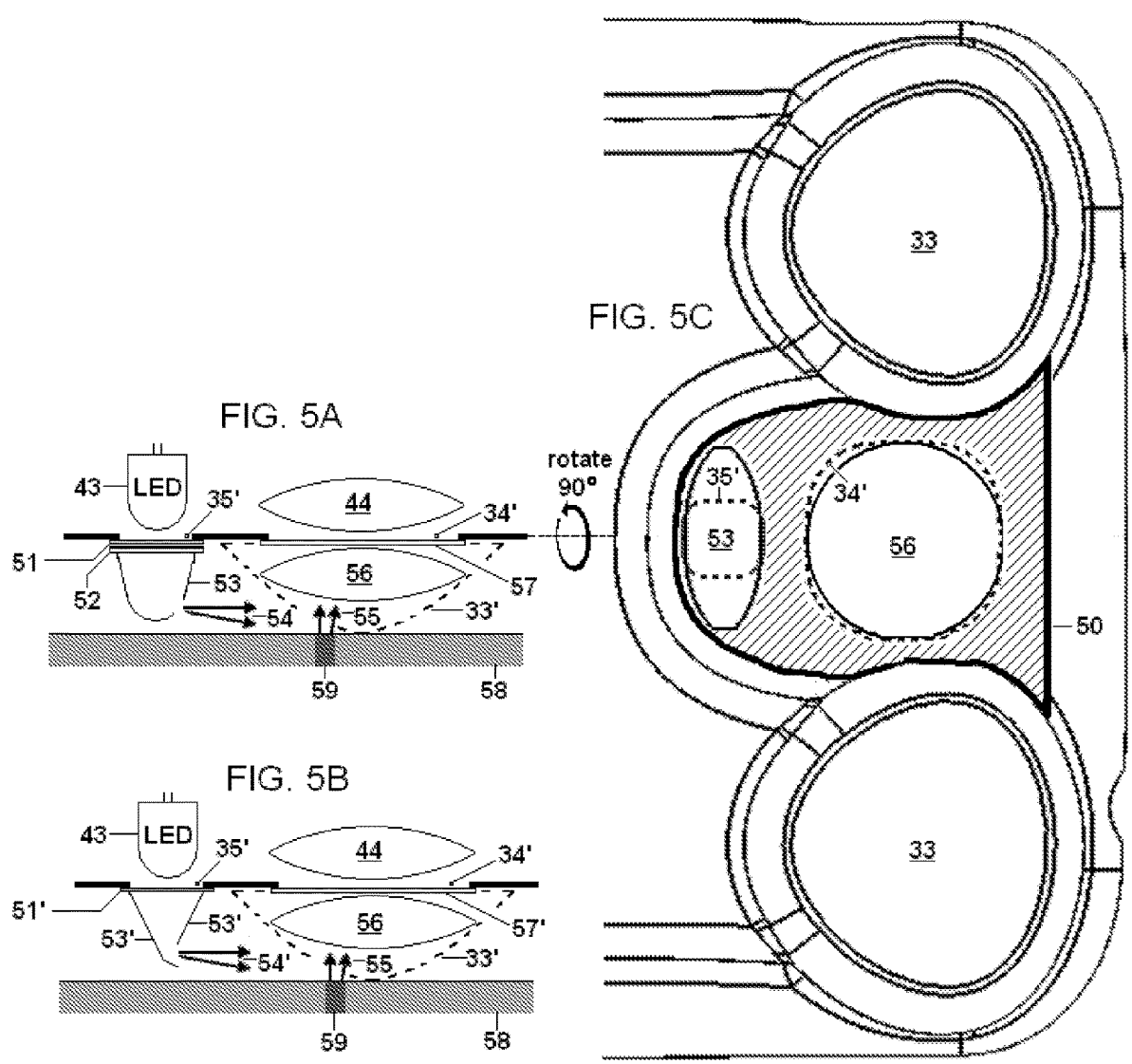

FIG. 10
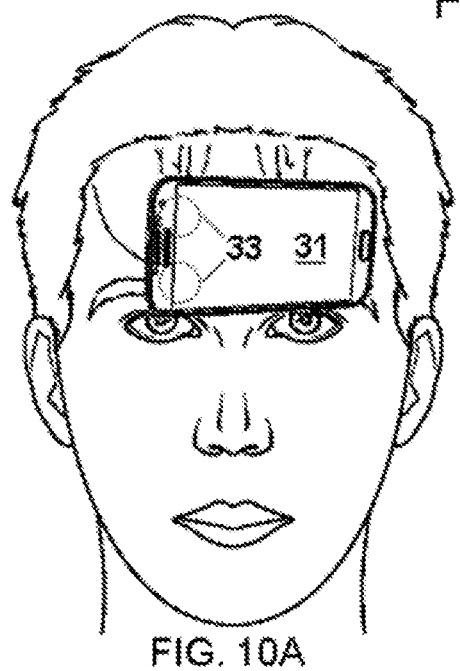
FIG. 10A
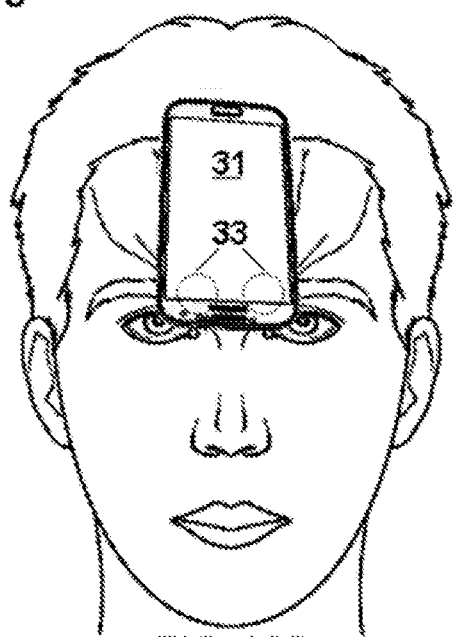
FIG. 10B
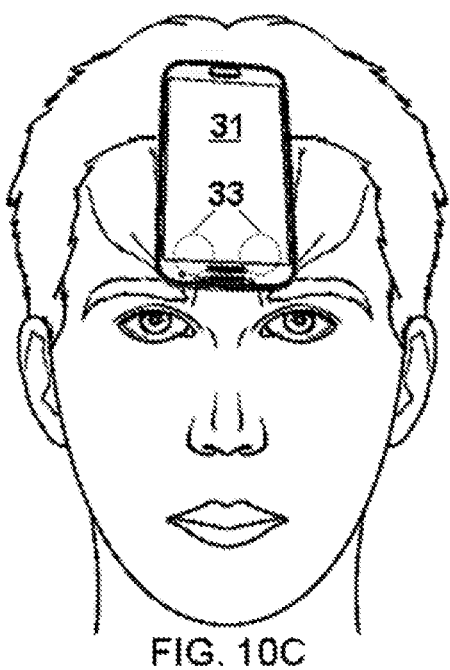
FIG. 10C
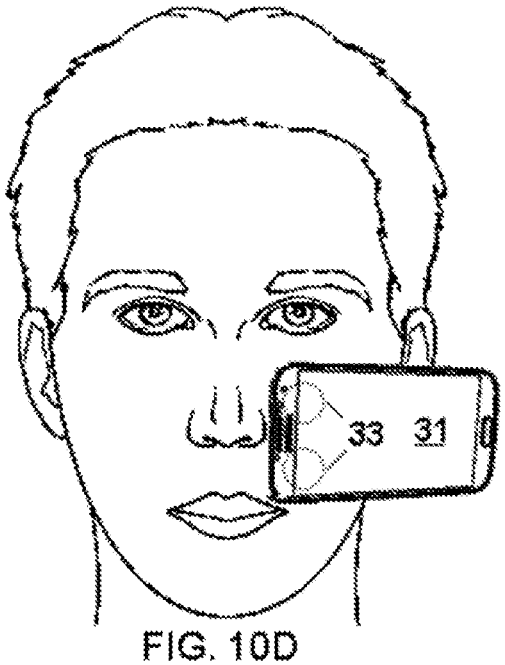
FIG. 10D

MOBILE PHONE FOR STIMULATING THE TRIGEMINAL NERVE TO TREAT DISORDERS

CROSS REFERENCE TO RELATED APPLICATIONS

This application is a Divisional of U.S. Nonprovisional application Ser. No. 14/337,059 filed 21 Jul. 2014; which is a (1) Continuation in Part of U.S. Nonprovisional application Ser. No. 14/292,491 filed 30 May 2014, now U.S. Pat. No. 9,375,571 issued 28 Jun. 2016; which claims the benefit of U.S. Provisional Application Ser. No. 62/001,004 filed 20 May 2014; and (2) is a Continuation-in-Part of U.S. Nonprovisional application Ser. No. 13/858,114 filed 8 Apr. 2013, now U.S. Pat. No. 9,248,286 issued 2 Feb. 2016: which claims the benefit of U.S. Provisional Application Ser. No. 61/752,895 filed 15 Jan. 2013; each of which is incorporated herein by reference in its entirety for all purposes.

BACKGROUND OF THE INVENTION

The field of the present invention relates to the delivery of energy impulses (and/or fields) to bodily tissues for therapeutic purposes. The invention relates more specifically to devices and methods for treating medical conditions such as migraine headaches and related disorders, wherein the patient uses the devices and methods as self-treatment, without the direct assistance of a healthcare professional. The energy impulses (and/or fields) that are used to treat those conditions comprise electrical and/or electromagnetic energy, delivered non-invasively to the patient, particularly to a branch of the trigeminal nerve on the surface of the head of the patient.

The use of electrical stimulation for treatment of medical conditions is well known. The form of electrical stimulation with which the present disclosure is concerned is reversible, as distinguished from the use of irreversible electrical stimulation to thermally ablate or otherwise permanently destroy the functioning nerves. In the present disclosure, reversible electrical stimulation that modulates the activity of a nerve for therapeutic purposes is also known as neurostimulation.

One of the most successful applications of modern understanding of the electrophysiological relationship between muscle and nerves is the cardiac pacemaker. Although origins of the cardiac pacemaker extend back into the 1800's, it was not until 1950 that the first practical, albeit external and bulky, pacemaker was developed. The first truly functional, wearable pacemaker appeared in 1957, and in 1960, the first fully implantable pacemaker was developed. Around this time, it was also found that electrical leads could be connected to the heart through veins, which eliminated the need to open the chest cavity and attach the lead to the heart wall. In 1975 the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat. No. 6,738,667 to DENO, et al., the disclosure of which is incorporated herein by reference). Because the leads are implanted within the patient, the pacemaker is an example of an implantable medical device.

Another such example is electrical stimulation of the brain with implanted electrodes (deep brain stimulation), which has been approved for use in the treatment of various conditions, including pain and movement disorders such as essential tremor and Parkinson's disease [Joel S. PERL-MUTTER and Jonathan W. Mink. Deep brain stimulation. Annu. Rev. Neurosci 29 (2006): 229-257].

Another application of electrical stimulation of nerves is the treatment of radiating pain in the lower extremities by stimulating the sacral nerve roots at the bottom of the spinal cord [Paul F. WHITE, Shitong Li and Jen W. Chiu. Electroanalgesia: Its Role in Acute and Chronic Pain Management. Anesth Analg 92(2001):505-513; patent U.S. Pat. No. 6,871,099, entitled Fully implantable microstimulator for spinal cord stimulation as a therapy for chronic pain, to WHITEHURST, et al].

The form of neurostimulation that is most relevant to the present invention is the stimulation of peripheral nerves of the head, for the prevention and treatment of headaches and related disorders. Recent reviews of the state of this area of neurostimulation are as follows: Todd J. SCHWEDT. Neurostimulation for Primary Headache Disorders. Curr Neurol Neurosci Rep 9(2, 2009): 101-107; JENKINS B, Tepper S J. Neurostimulation for primary headache disorders, part 1: pathophysiology and anatomy, history of neuromodulation in headache treatment, and review of peripheral neuromodulation in primary headaches. Headache 51 (8, 2011): 1254-1266; MAGIS D, Schoenen J. Advances and challenges in neurostimulation for headaches. Lancet Neurol 11 (8, 2012): 708-719; JURGENS TP, Leone M. Pearls and pitfalls: neurostimulation in headache. Cephalalgia 33 (8, 2013): 512-525; Serge Y. RASSKAZOFF and Konstantin V. Slavin. Neuromodulation for cephalgias. Surg Neurol Int. 2013; 4 (Suppl 3): S136-S150; Giorgio LAMBRU and Manjit Singh Matharu. Peripheral neurostimulation in primary headaches. Neurological Sciences 35 (1 Supplement, 2014): 77-81.

Many such therapeutic applications of electrical stimulation involve the surgical implantation of electrodes within a patient. In contrast, devices used for the procedures that are disclosed here do not involve surgery, i.e., they are not implantable medical devices. Instead, the present devices and methods stimulate nerves by transmitting energy to nerves and tissue non-invasively. A medical procedure is defined as being non-invasive when no break in the skin (or other surface of the body, such as a wound bed) is created through use of the method, and when there is no contact with an internal body cavity beyond a body orifice (e.g., beyond the mouth or beyond the external auditory meatus of the ear). Such non-invasive procedures are distinguished from invasive procedures (including minimally invasive procedures) in that the invasive procedures insert a substance or device into or through the skin (or other surface of the body, such as a wound bed) or into an internal body cavity beyond a body orifice.

For example, transcutaneous electrical stimulation of a nerve is non-invasive because it involves attaching electrodes to the skin, or otherwise stimulating at or beyond the surface of the skin or using a form-fitting conductive garment, without breaking the skin [Thierry KELLER and Andreas Kuhn. Electrodes for transcutaneous (surface) electrical stimulation. Journal of Automatic Control, University of Belgrade 18 (2, 2008): 35-45; Mark R. PRAUSNITZ. The effects of electric current applied to skin: A review for transdermal drug delivery. Advanced Drug Delivery Reviews 18 (1996) 395-425]. In contrast, percutaneous electrical stimulation of a nerve is minimally invasive because it involves the introduction of an electrode under the skin, via needle-puncture of the skin.

Another form of non-invasive electrical stimulation is magnetic stimulation. It involves the induction, by a time-varying magnetic field, of electrical fields and current within tissue, in accordance with Faraday's law of induction.

Magnetic stimulation is non-invasive because the magnetic field is produced by passing a time-varying current through a coil positioned outside the body. An electric field is induced at a distance, causing electric current to flow within electrically conducting bodily tissue. The electrical circuits for magnetic stimulators are generally complex and expensive and use a high current impulse generator that may produce discharge currents of 5,000 amps or more, which is passed through the stimulator coil to produce a magnetic pulse. The principles of electrical nerve stimulation using a magnetic stimulator, along with descriptions of medical applications of magnetic stimulation, are reviewed in: Chris HOVEY and Reza Jalinous, The Guide to Magnetic Stimulation, The Magstim Company Ltd, Spring Gardens, Whitland, Carmarthenshire, SA34 0 HR, United Kingdom, 2006. In contrast, the magnetic stimulators that have been disclosed by the present Applicant are relatively simpler devices that use considerably smaller currents within the stimulator coils. Accordingly, they are intended to satisfy the need for simple-to-use and less expensive non-invasive magnetic stimulation devices.

Potential advantages of such non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures are generally painless and may be performed without the dangers and costs of surgery. They are ordinarily performed even without the need for local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace. Furthermore, the cost of non-invasive procedures may be significantly reduced relative to comparable invasive procedures.

In co-pending, commonly assigned patent applications, Applicant disclosed noninvasive electrical nerve stimulation devices, which are adapted, and for certain applications improved, in the present disclosure [application Ser. No. 13/183,765 and Publication US2011/0276112, entitled Devices and methods for non-invasive capacitive electrical stimulation and their use for vagus nerve stimulation on the neck of a patient, to SIMON et al.; application Ser. No. 12/964,050 and Publication US2011/0125203, entitled Magnetic Stimulation Devices and Methods of Therapy, to SIMON et al.; and other co-pending commonly assigned applications that are cited therein, which are hereby incorporated by reference in the present application]. The present disclosure elaborates on the electrical stimulation device, rather than the magnetic stimulation device that has similar functionality, with the understanding that unless it is otherwise indicated, the elaboration could apply to either the electrical or the magnetic nerve stimulation device. Because the earlier devices have already been disclosed, the present disclosure focuses on what is new with respect to the earlier disclosures.

In the present disclosure, the patient ordinarily applies the stimulator to himself or herself, without the benefit of having a trained healthcare provider nearby. The primary advantage of the self-stimulation therapy is that it can be administered more or less immediately when symptoms occur, rather than having to visit the healthcare provider at a clinic or emergency room. The need for such a visit would only compound the aggravation that the patient is already experiencing. Another advantage of the self-stimulation therapy is the convenience of providing the therapy in the patient's home or workplace, which eliminates scheduling difficulties, for example, when the nerve stimulation is being administered for prophylactic reasons at odd hours of the day. Furthermore, the cost of the treatment may be reduced by not requiring the involvement of a trained healthcare provider.

An exemplary teaching of the present invention is the treatment of migraine and other primary headaches such as cluster headaches, including sinus symptoms ("sinus" headaches) irrespective of whether those symptoms arise from an allergy that is co-morbid with the headache. However, it is understood that electrical stimulation by the disclosed methods and devices may be used to treat other conditions as well, including conditions described in the cited co-pending, commonly assigned patent applications.

Chronic daily headache by definition occurs with a frequency of at least 15 headache days per month for greater than 3 months duration. Chronic migraine sufferers comprise a subset of the population of chronic headache sufferers, as do those who suffer other primary headache disorders such as chronic tension-type headache [Bert B. VARGAS, David W. Dodick. The Face of Chronic Migraine: Epidemiology, Demographics, and Treatment Strategies. Neurol Clin 27 (2009) 467-479; Peter J. GOADSBY, Richard B. Lipton, Michel D. Ferrari. Migraine—Current understanding and treatment. N Engl J Med 346 (4, 2002): 257-270; Stephen D SILBERSTEIN. Migraine. LANCET 363 (2004): 381-391].

A migraine headache typically passes through the following stages: prodrome, aura, headache pain, and postdrome. All these phases do not necessarily occur, and there is not necessarily a distinct onset or end of each stage, with the possible exception of the aura. An interictal period follows the postdrome, unless the postdrome of one migraine attack overlaps the prodrome of the next migraine attack.

The prodrome stage comprises triggering events followed by premonitory symptoms. The prodrome is often characterized by fatigue, sleepiness, elation, food cravings, depression, and irritability, among other symptoms. Triggers (also called precipitating factors) such as excessive stress or sensory barrage usually precede the attack by less than 48 h. The average duration of the prodrome is 6 to 10 hours, but in half of migraine attacks, the prodrome is less than two hours (or absent), and in approximately 15% of migraine attacks, the prodrome lasts for 12 hours to 2 days.

The aura is due to cortical spreading depression within the brain. Approximately 20-30% of migraine sufferers experience an aura, ordinarily a visual aura, which is perceived as a scintillating scotoma (zig-zag line) that moves within the visual field. However, aura symptoms, regardless of their form, vary to a great extent in duration and severity from patient to patient, and also within the same individual.

Although the headache phase can begin at any hour, it most commonly begins as mild pain when the patient awakens in the morning. It then gradually builds at variable rates to reach a peak at which the pain is usually described as moderate to severe. Migraine headaches often occur on both sides of the head in children, but an adult pattern of unilateral pain often emerges in adolescence. The pain is often reported as starting in the occipital/neck regions, later becoming frontotemporal. It is throbbing and aggravated by physical effort, with all stimuli tending to accentuate the headache. The pain phase lasts 4-72 h in adults and 1-72 h in children, with a mean duration generally of less than 1 day. The pain intensity usually follows a smooth curve with a crescendo with a diminuendo. After the headache has resolved, many patients are left with a postdrome that lingers for one to two days. The main complaints during the prodrome are cognitive difficulties, such as mental tiredness.

For the present medical applications, an electrical stimulator device is ordinarily applied to branches of the trigeminal nerve that lie close to the patient's skin. Noninvasive trigeminal-branch electrical stimulators have been studied in connection with the treatment of headache, but the satisfaction of patients with such devices has been equivocal, with almost 47% of the patients reporting dissatisfaction with the devices [MAGIS D, Sava S, D Elia T S, Baschi R, Schoenen J. Safety and patients' satisfaction of transcutaneous Supraorbital NeuroStimulation (tSNS) with the Cefaly® device in headache treatment: a survey of 2,313 headache sufferers in the general population. J Headache Pain. 14 (1, 2013): 95, pp. 1-8]. The present invention will increase satisfaction of patients with regard to headache prevention and with regard to usefulness in terminating headaches that are in progress. As disclosed herein, a method for improving the nerve stimulation is to increase the stimulation current density in small areas near the sites where nerves emerge near the skin surface from deeper neural tissue, thereby stimulating the whole nerve rather than downstream branches, and avoiding the stimulation of muscle and nerves in the skin that produce pain.

A related trigeminal disorder that may be treated with the present invention is trigeminal neuralgia, also known as tic douloureux. Trigeminal neuralgia is one of the worst symptoms experienced by people with multiple sclerosis. Presently available noninvasive electrical stimulators are of limited value in that regard because they treat only one branch of the trigeminal nerve (V1) that is infrequently associated with the neuralgia [Luke BENNETTO, Nikunj K Patel, Geraint Fuller. Trigeminal neuralgia and its management. BMJ 334 (7586, 2007): 201-205]. An advantage of the present invention is that it may be used to treat nerves corresponding to all three main branches of the trigeminal nerve, in each case by increasing the stimulation current density in small areas near the sites where a nerve emerge near the skin surface from deeper neural tissue. Yet another advantage of the disclosed methods and devices is that they may also be used to treat trigeminal neuropathies, which are disorders characterized and manifesting as skin and mucosal numbness in the region innervated by the trigeminal nerve (not necessarily involving pain) [SMITH J H, Cutrer F M. Numbness matters: a clinical review of trigeminal neuropathy. Cephalalgia 31 (10, 2011): 1131-1144].

For more background information on the use of noninvasive nerve stimulation to treat migraine/sinus headaches, refer to co-pending, commonly assigned application number U.S. Ser. No. 13/109,250 with publication number US20110230701, entitled Electrical and magnetic stimulators used to treat migraine/sinus headache and comorbid disorders to SIMON et al; and application number U.S. Ser. No. 13/183,721 with publication number US20110276107, entitled Electrical and magnetic stimulators used to treat migraine/sinus headache, rhinitis, sinusitis, rhinosinusitis, and comorbid disorders, to SIMON et al, which are incorporated by reference.

Despite the advantages of having a patient administer the nerve stimulation by him or herself, such self-stimulation presents certain risks and difficulties relating to safety and efficacy. In some situations, the nerve stimulator should be applied to the left or to the right side of the face, but not vice versa. Similarly, because there are many different nerves on the face, the patient may unintentionally or deliberately stimulate a nerve other than the prescribed one. Therefore, if the patient is using the nerve stimulator by himself or herself, it would be useful for the device be designed so that it can be used only to stimulate the prescribed nerve(s). The present invention discloses methods for preventing stimulation of the wrong nerve.

Another issue concerns the positioning of the nerve stimulator on the face of the patient. Although the stimulator is designed to be robust against very small variations in position of the stimulator relative to the prescribed nerve, there is nevertheless an optimal position that would preferably be maintained throughout the stimulation session in order to achieve maximum effectiveness from the stimulation. The patient will sense whether the nerve is being stimulated and can adjust the position of the stimulator in search for the optimum, but the patient also has the option of adjusting the amplitude of the stimulation in an attempt to compensate for a sub-optimal position. However, the ability to compensate using stimulation-amplitude control is limited by the likelihood that the skin and other tissue in the vicinity of the nerve may become uncomfortable if the amplitude of stimulation becomes too high.

A related problem is that fluctuating movement of the stimulator relative to nerve being stimulated is to some extent unavoidable, due for example to neck and face muscle contractions that accompany breathing. The combination of sub-optimal positioning of the device on the patient's skin and unavoidable small movement of the device makes it difficult to assure that the patient is receiving exactly the prescribed stimulation dose in each stimulation session.

Another problem is that the patient may wish to stop the stimulation session based only on some subjective assessment of whether the stimulation has sufficiently relieved the symptoms. However, there may be a diminishing effectiveness if the stimulation session is too long, for the following reason. Let the numerical value of the accumulated effects of prescribed nerve stimulation be denoted as S(t). It may for present exemplary purposes be represented as a function that increases at a rate proportional to the stimulation voltage V in the vicinity of the nerve and decays with a time constant $\tau_P$, such that after prolonged stimulation, the accumulated stimulation effectiveness may saturate at a value equal to the product of V and $\tau_P$. Thus, if $T_P$ is the duration of a nerve stimulation in a particular treatment session, then for time t<$T_P$, $S(t)=V\tau_P[1-\exp(-t/\tau_P)]+S_0 \exp(-t/\tau_P)$, and for t>$T_P$, $S(t)=S(T_P)\exp(-[t-T_P]/\tau_P)$, where the time t is measured from the start of a stimulus, and S0 is the value of S when t=0. The optimal duration of a stimulation session may be different from patient to patient, because the decay time constant $\tau_P$ may vary from patient to patient. To the extent that the stimulation protocol is designed to treat each patient individually, such that subsequent treatment sessions are designed in view of the effectiveness of previous treatment sessions, it is would be useful for the stimulation amplitude V be as constant as possible, and the treatment session should take into account the above-mentioned principle of diminishing returns. At a minimum, the average stimulation amplitude in a session should be estimated or evaluated, despite movement of the stimulator relative to the nerve and despite amplitude adjustment by the patient.

These potential problems, related to placement and movement of the stimulator, do not arise in patients in whom a stimulator electrode has been implanted about a nerve of the head. They are also of minor significance in situations where a healthcare provider is responsible for careful usage of noninvasive stimulator devices, rather than the patient. More generally, when the patient performs self-stimulation with the nerve stimulator, practical matters arise such as: how to maintain and charge the stimulator device, how to enable the patient to initiate a stimulation session, how to design the stimulation session based on the present medical circumstances of the patient, how to monitor operation of the device taking into account all of the factors that may influence a successful treatment session, and how to evaluate the success of the treatment session when it is finished. Furthermore, when the patient is able to perform self-stimulation, administrative matters such as maintaining medical records and billing should be addressed. The present invention is intended to address many such problems. The invention comprises several components, each of which may be involved in the solution of different problems, such that the system as a whole is more functional than the component parts considered individually.

SUMMARY OF THE INVENTION

The present invention involves devices and methods for the self-treatment of diseases and/or disorders by a patient through electrical stimulation of one or more nerves within the patient. Devices are disclosed that allow the stimulation to be performed noninvasively, wherein electrodes are placed against the skin of the patient. In preferred embodiments of the invention, the selected nerve is a branch of the trigeminal nerve that passes near the surface of the skin, such as the supraorbital and supratrochlear nerves. However, other nerves of the head may also be stimulated using the disclosed methods, such as the greater occipital, lesser occipital, and great auricular nerves. The disclosure uses the prevention and treatment of migraine headaches as the exemplary medical condition. However, other headache types, trigeminal neuralgia, trigeminal neuropathy, facial pain (e.g., dental pain) and their co-morbid disorders may also be treated using the disclosed methods and devices.

In one aspect of the invention, a nerve stimulation system comprises a mobile phone that can be used for dual purposes: (1) as a phone, such as a smartphone that would contain all of the typical features of such a phone (e.g., voice communication, Wi-Fi, web browsing, texting, email connectivity, etc.); and (2) as a nerve stimulation device incorporated into, or joined to and electrically connected with, the mobile phone. The nerve stimulation device preferably comprises one or more electrodes extending from an outer surface of the phone housing. The electrodes are configured to apply one or more electrical impulses through the surface of a patient's skin to a selected nerve within the patient. A signal generator is coupled to the electrodes for applying the electrical impulses to the electrodes, and a power source is coupled to the signal generator and/or the electrodes for providing power.

In one embodiment, the waveform of the signal that is to be applied to the patient is first created in a device exterior to, and remote from, the mobile phone housing. The mobile phone preferably includes a software application that can be downloaded into the phone to receive the waveform from the exterior device and then provide the electrical waveform signal to the electrodes. In certain embodiments, the system further includes an amplifier coupled to the electrodes to amplify the signal generated by the application software and then apply the amplified signal to the electrodes. The amplifier may be incorporated into the phone, or joined to and connected to the phone, or it may be a separate device that can be plugged into the phone to couple the amplifier with the software application and the electrodes. In one embodiment, the amplifier includes a connector that connects to the earphone jack socket in the mobile phone, amplifying a pseudo-audio stereo waveform signal that is produced by the smartphone, and driving the electrodes with that signal.

The system is designed to address particular problems that arise during self-treatment, when a medical professional is not present. Such problems include ensuring that the patient stimulates the prescribed nerve, minimizing or documenting motion of the stimulator, documenting the patient's adjustment of the stimulation amplitude, and controlling the amount of energy that can be delivered to the patient during a stimulation session.

In one embodiment of the invention, the smartphone's rear camera is used to image fluorescent spots that had been applied to reference positions on the patient's skin above the selected nerve. During repeated sessions of the nerve stimulation, the position and orientation of the stimulator are adjusted in such a way that fluorescent spots that are imaged by the camera appear in the same way during the successive sessions. Movement of the imaged fluorescent spots may also be used to assess the extent to which the stimulator is fluctuating in position during the course of a stimulation session.

The parameters for the protocol of each stimulation session may be transmitted from an external device to the stimulator device from a physician-controlled computer, which provides authorization for the recharging of the stimulator device's batteries by a base station (typically a laptop computer). Parameters of the stimulation protocol may be varied in response to heterogeneity in the symptoms of patients. Different stimulation parameters may also be selected as the course of the patient's medical condition changes. In preferred embodiments, the disclosed stimulation methods and devices do not produce clinically significant side effects, such as agitation or anxiety, or changes in heart rate or blood pressure.

In a preferred embodiment of the invention, the stimulator housing comprises a rechargeable source of electrical power and two or more electrodes that are configured to stimulate a nerve of varying depth. The stimulator may comprise two electrodes that lie on both sides of the hand-held stimulator housing. Each electrode may be in continuous contact with an electrically conducting medium that extends from the patient-interface stimulation element of the stimulator to the electrode. The interface element contacts the patient's skin when the device is in operation.

Current passing through an electrode may be from about 0 to about 40 mA, with voltage across the electrodes from about 0 to about 30 volts. The current is passed through the electrodes in bursts of pulses. There may be from about 1 to about 20 pulses per burst, preferably about five pulses. Each pulse within a burst has a duration from about 20 to about 1000 microseconds, preferably about 200 microseconds. A burst followed by a silent inter-burst interval repeats from at about 1 to about 5000 bursts per second (bps, similar to Hz), preferably from at about 15 to about 50 bps, and even more preferably at about 25 bps. The preferred shape of each pulse is a full sinusoidal wave.

A source of power supplies a pulse of electric charge to the electrodes, such that the electrodes produce an electric current and/or an electric field within the patient. The electrical stimulator is configured to induce a peak pulse voltage sufficient to produce an electric field in the vicinity of the selected nerve, to cause the nerve to depolarize and reach a threshold for action potential propagation. By way of example, the threshold electric field for stimulation of the nerve may be about 8 V/m at about 1000 Hz. For example, the device may produce an electric field within the patient from about 10 to about 600 V/m (preferably less than about 100 V/m) and an electrical field gradient of greater than about 2 V/m/mm. Electric fields that are produced at a nerve are generally sufficient to excite all myelinated A and B fibers, but not necessarily the unmyelinated C fibers. However, by using a reduced amplitude of stimulation, excitation of A-delta and B fibers may also be avoided.

The preferred stimulator shapes an elongated electric field of effect that can be oriented parallel to a long nerve. By selecting a suitable waveform to stimulate the nerve, along with suitable parameters such as current, voltage, pulse width, pulses per burst, inter-burst interval, etc., the stimulator produces a correspondingly selective physiological response in an individual patient. Such a suitable waveform and parameters are simultaneously selected to avoid substantially stimulating nerves and tissue other than the target nerve, particularly avoiding the stimulation of nerves in the skin that produce pain.

In a preferred embodiment of the invention, the stimulator comprises two electrodes that lie side-by-side within separate stimulator assemblies, wherein the electrodes are separated by electrically insulating material. Each electrode and the patient's skin are connected electrically through an electrically conducting medium that extends from the skin to the electrode. The position and angular orientation of the device are adjusted about a location on the skin until the patient perceives stimulation when current is passed through the stimulator electrodes. The applied current is increased gradually, first to a level wherein the patient feels sensation from the stimulation. The power is then increased, but is set to a level that is less than one at which the patient first indicates any discomfort. The stimulator signal waveform may have a frequency and other parameters that are selected to produce a therapeutic result in the patient.

A method for treating a patient with a medical condition according to the invention comprises generating an electrical signal sufficient to modulate a trigeminal nerve within the patient, wirelessly transmitting the electric signal to a handheld mobile device (such as a mobile phone), contacting an outer surface of a head of the patient with a contact surface of the mobile device and applying one or more electrical impulses to the outer surface of the patient's skin such that the electrical impulses pass through the patient's skin transcutaneously to the trigeminal nerve. The electric impulses are sufficient to modulate the nerve and cause the release of inhibitory neurotransmitters in the brain of the patient to treat the medical condition.

In one aspect of the invention, the contacting step is carried out by applying the contact surfaces of the mobile device to branches of the trigeminal nerve that lie close to the patient's skin. The present invention will increase satisfaction of patients with regard to headache prevention and with regard to usefulness in terminating headaches that are in progress. As disclosed herein, a method for improving the nerve stimulation is to increase the stimulation current density in small areas near the sites where nerves emerge near the skin surface from deeper neural tissue, thereby stimulating the whole nerve rather than downstream branches, and avoiding the stimulation of muscle and nerves in the skin that produce pain.

In one embodiment, the method of the present invention may be used to treat trigeminal neuralgia. An advantage of the present invention is that it may be used to treat nerves corresponding to all three main branches of the trigeminal nerve, in each case by increasing the stimulation current density in small areas near the sites where a nerve emerge near the skin surface from deeper neural tissue. Yet another advantage of the disclosed methods and devices is that they may also be used to treat trigeminal neuropathies, which are disorders characterized and manifesting as skin and mucosal numbness in the region innervated by the trigeminal nerve.

In some situations, the nerve stimulator should be applied to the left or to the right side of the face, but not vice versa. Similarly, because there are many different nerves on the face, the patient may unintentionally or deliberately stimulate a nerve other than the prescribed one. Therefore, if the patient is using the nerve stimulator by himself or herself, it would be useful for the device be designed so that it can be used only to stimulate the prescribed nerve(s). The present invention discloses methods for preventing stimulation of the wrong nerve.

In yet another embodiment, the method of the present invention comprises sensing whether the trigeminal nerve has been stimulated and providing feedback to the patient. This allows the patient to adjust the position of the mobile device and/or the amplitude of the electric current to optimize the treatment.

The novel systems, devices and methods for treating medical condition such as migraine headache are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference. If any disclosures are incorporated herein by reference and such disclosures conflict in part and/or in whole with the present disclosure, then to the extent of conflict, and/or broader disclosure, and/or broader definition of terms, the present disclosure controls. If such disclosures conflict in part and/or in whole with one another, then to the extent of conflict, the later-dated disclosure controls.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 1 shows a schematic view of nerve modulating devices according to the present invention, which supply controlled pulses of electrical current to surface electrodes;

FIG. 3A is a front view of a dual-electrode stimulator according to an embodiment of the present invention, showing that the stimulator device comprises a smartphone;

FIG. 3B is a back view of the dual-electrode stimulator shown in FIG. 3A;

FIG. 3C is a side view of the dual-electrode stimulator shown in FIG. 3A;

FIG. 5A illustrates a cross-sectional view of an optical assembly used to shift illumination of a smartphone flash LED from visible to infrared light and to use that infrared light to excite and image fluorescence from material placed in the patient's skin;

FIG. 5B illustrates a cross-sectional view of an optical assembly used to excite and image fluorescence from material placed in the patient's skin, when the shifting of the wavelength of LED light is not needed;

FIG. 5C rotates the view shown in FIG. 5A by 90 degrees, showing where the optical assembly is snapped into the stimulator between the electrode surfaces;

FIG. 10A and FIG. 10B illustrate unilateral and bilateral stimulation, respectively, of the supraorbital and supratrochlear nerves, when one or two electrodes, respectively, of the stimulator are applied in the vicinity of supraorbital and supratrochlear foramen or notches;

FIG. 10C shows the bilateral stimulation with the electrodes positioned higher on the forehead;

FIG. 10D and FIG. 10E show stimulation of the infraorbital nerve when one of the electrodes is applied in the vicinity of the infraorbital foramen;

DETAILED DESCRIPTION OF THE PREFERRED EMBODIMENTS

Figure 2A:
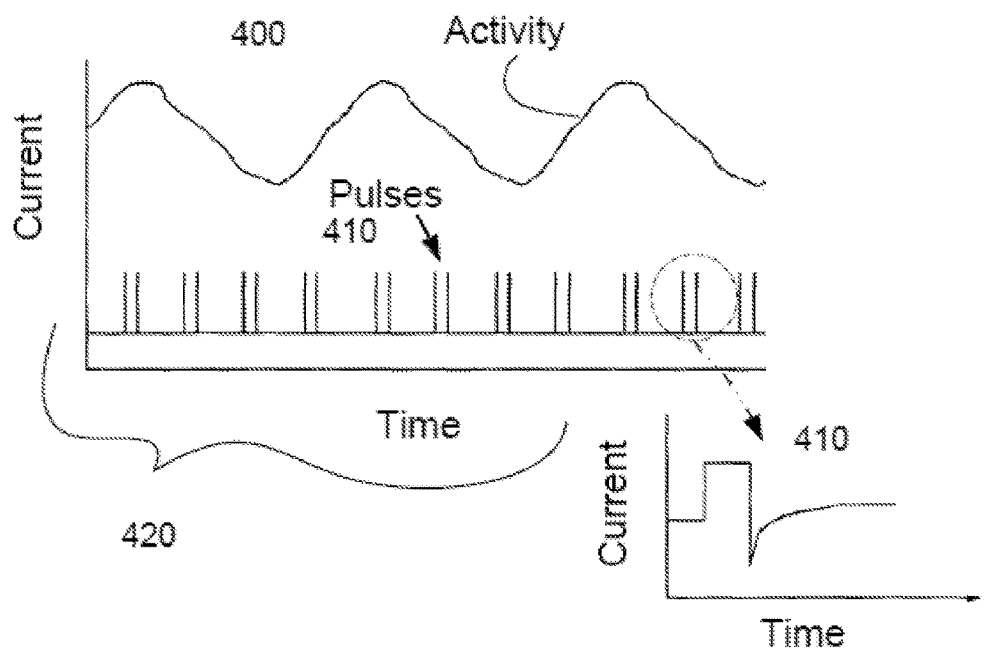
FIG. 2A shows an exemplary electrical voltage/current profile for stimulating and/or modulating impulses that are applied to a nerve according to the present invention.

In the present invention, electrodes applied to the skin of the patient generate currents within the tissue of the patient. An objective of some embodiments of the invention is to produce and apply the electrical impulses so as to interact with the signals of one or more nerves, in order to achieve the therapeutic result. Much of the disclosure will be directed specifically to treatment of a patient by stimulation in or around a branch of the trigeminal nerve, with devices positioned non-invasively on a patient's head. However, it will also be appreciated that the devices and methods of the present invention can be applied to other tissues and nerves of the body, including but not limited to other parasympathetic nerves, sympathetic nerves, spinal or other cranial nerves.

Although the present invention is particularly focused on the treatment of headache disorders, including but not limited to migraine, tension type headache, chronic headache, cluster headache and/or occipital neuralgia, it will also be appreciated that the devices and methods of the present invention can be applied to other tissues and nerves of the body, including but not limited to other parasympathetic nerves, sympathetic nerves, spinal or cranial nerves. In addition, stimulation of the trigeminal nerve may also result in other benefits to the patient such as: relaxation of the smooth muscle of the bronchia for treatment of bronchoconstriction associated with asthma, COPD and/or exercised-induced bronchoconstriction, increase in blood pressure associated with orthostatic hypotension, reduction in blood pressure that may be associated with, for example, refractory hypertension, treating ileus conditions, neuropsychiatric disorders, such as depression, anxiety and/or personality disorders, anaphylaxis, obesity and/or type II diabetes, seizures, such as epileptic seizures, migraine, tension-type, cluster, MOH and other types of headache, rhinitis, sinusitis, atrial fibrillation, autism, modulation of liver function, gastroparesis and other functional gastrointestinal disorders, movement disorders, CHF, chronic pain, fibromyalgia, metabolic or thyroid disorders and/or cardiovascular disease. Such treatments for different disorders are disclosed in the following US patent applications assigned to ElectroCore, LLC (the complete disclosures of which are incorporated by reference in their entirety for all purposes): U.S. patent application Ser. No. 13/858,114, filed Apr. 8, 2013 (ELEC-47), U.S. patent application Ser. No. 13/783,391, filed Mar. 3, 2013 (ELEC-49), U.S. patent application Ser. No. 13/736,096, filed Jan. 8, 2013 (ELEC-43), U.S. patent application Ser. No. 13/731,035, filed Dec. 30, 2012 (ELEC-46), U.S. patent application Ser. No. 13/603,799 filed Sep. 5, 2012 (ELEC-44-1), U.S. patent application Ser. No. 13/357,010, filed Jan. 24, 2012 (ELEC-41), U.S. patent application Ser. No. 13/279,437 filed Oct. 24, 2011 (ELEC-40), U.S. patent application Ser. No. 13/222,087 filed Aug. 31, 2011 (ELEC-39), U.S. patent application Ser. No. 13/183,765 filed Jul. 15, 2011 (ELEC-38), U.S. patent application Ser. No. 13/183,721 filed Jul. 15, 2011, now U.S. Pat. No. 8,676,330 issued Mar. 18, 2014 (ELEC-36), U.S. patent application Ser. No. 13/109,250 filed May 17, 2011, now U.S. Pat. No. 8,676,324 issued Mar. 18, 2014 (ELEC-37), U.S. patent application Ser. No. 13/075,746 filed Mar. 30, 2011 (ELEC-35), U.S. patent application Ser. No. 13/024,727, filed Feb. 10, 2011 (ELEC-34), U.S. patent application Ser. No. 13/005,005 filed Jan. 12, 2011 (ELEC-33), U.S. patent application Ser. No. 12/964,050 filed Dec. 9, 2010 (ELEC-32), U.S. patent application Ser. No. 12/859,568 filed Aug. 9, 2010 (ELEC-31), U.S. patent application Ser. No. 12/408,131 filed Mar. 20, 2009 (ELEC-17CP1) and U.S. patent application Ser. No. 12/612,177 filed Nov. 9, 2009 now U.S. Pat. No. 8,041,428 issued Oct. 18, 2011 (ELEC-14CP1).

Description of the Nerve Stimulating/Modulating Devices

Devices of the invention that are used to stimulate a branch of the trigeminal nerve will now be described. An embodiment of the present invention is shown in FIG. 1, which is a schematic diagram of an electrode-based nerve stimulating/modulating device 302 for delivering impulses of energy to nerves for the treatment of medical conditions. As shown, device 302 may include an impulse generator 310; a power source 320 coupled to the impulse generator 310; a control unit 330 in communication with the impulse generator 310 and coupled to the power source 320; and electrodes 340 coupled via wires 345 to impulse generator 310. In a preferred embodiment, the same impulse generator 310, power source 320, and control unit 330 may be used for either a magnetic stimulator or the electrode-based stimulator 302, allowing the user to change parameter settings depending on whether magnetic coils or the electrodes 340 are attached.

Although a pair of electrodes 340 is shown in FIG. 1, in practice the electrodes may also comprise three or more distinct electrode elements, each of which is connected in series or in parallel to the impulse generator 310. Thus, the electrodes 340 that are shown in FIG. 1 represent all electrodes of the device collectively.

The item labeled in FIG. 1 as 350 is a volume, contiguous with an electrode 340, that is filled with electrically conducting medium. The conducting medium in which the electrode 340 is embedded need not completely surround an electrode. The volume 350 is electrically connected to the patient at a target skin surface in order to shape the current density passed through an electrode 340 that is needed to accomplish stimulation of the patient's nerve or tissue. The electrical connection to the patient's skin surface is through an interface 351. In one embodiment, the interface is made of an electrically insulating (dielectric) material, such as a thin sheet of Mylar. In that case, electrical coupling of the stimulator to the patient is capacitive. In other embodiments, the interface comprises electrically conducting material, such as the electrically conducting medium 350 itself, an electrically conducting or permeable membrane, or a metal piece. In that case, electrical coupling of the stimulator to the patient is ohmic. As shown, the interface may be deformable such that it is form fitting when applied to the surface of the body. Thus, the sinuousness or curvature shown at the outer surface of the interface 351 corresponds also to sinuousness or curvature on the surface of the body, against which the interface 351 is applied, so as to make the interface and body surface contiguous.

The control unit 330 controls the impulse generator 310 to generate a signal for each of the device's electrodes (or magnetic coils). The signals are selected to be suitable for amelioration of a particular medical condition, when the signals are applied non-invasively to a target nerve or tissue via the electrodes 340. It is noted that nerve stimulating/modulating device 302 may be referred to by its function as a pulse generator. Patent application publications US2005/0075701 and US2005/0075702, both to SHAFER, contain descriptions of pulse generators that may be applicable to the present invention. By way of example, a pulse generator is also commercially available, such as Agilent 33522A Function/Arbitrary Waveform Generator, Agilent Technologies, Inc., 5301 Stevens Creek Blvd Santa Clara Calif. 95051.

The control unit 330 may also comprise a general purpose computer, comprising one or more CPU, computer memories for the storage of executable computer programs (including the system's operating system) and the storage and retrieval of data, disk storage devices, communication devices (such as serial and USB ports) for accepting external signals from a keyboard, computer mouse, and touchscreen, as well as any externally supplied physiological signals (see FIG. 11), analog-to-digital converters for digitizing externally supplied analog signals (see FIG. 11), communication devices for the transmission and receipt of data to and from external devices such as printers and modems that comprise part of the system, hardware for generating the display of information on monitors or display screens that comprise part of the system, and busses to interconnect the above-mentioned components. Thus, the user may operate the system by typing or otherwise providing instructions for the control unit 330 at a device such as a keyboard or touchscreen and view the results on a device such as the system's computer monitor or display screen, or direct the results to a printer, modem, and/or storage disk. Control of the system may be based upon feedback measured from externally supplied physiological or environmental signals. Alternatively, the control unit 330 may have a compact and simple structure, for example, wherein the user may operate the system using only an on/off switch and power control wheel or knob, or their touchscreen equivalent. In a section below, an embodiment is also described wherein the stimulator housing has a simple structure, but other components of the control unit 330 are distributed into other devices (see FIG. 7).

Parameters for the nerve or tissue stimulation include power level, frequency and train duration (or pulse number). The stimulation characteristics of each pulse, such as depth of penetration, strength and selectivity, depend on the rise time and peak electrical energy transferred to the electrodes, as well as the spatial distribution of the electric field that is produced by the electrodes. The rise time and peak energy are governed by the electrical characteristics of the stimulator and electrodes, as well as by the anatomy of the region of current flow within the patient. In one embodiment of the invention, pulse parameters are set in such as way as to account for the detailed anatomy surrounding the nerve that is being stimulated [Bartosz SAWICKI, Robert Szmurlo, Przemyslaw Plonecki, Jacek Starzyński, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE '07. Amsterdam, IOS Press, 2008]. Pulses may be monophasic, biphasic or polyphasic. Embodiments of the invention include those that are fixed frequency, where each pulse in a train has the same inter-stimulus interval, and those that have modulated frequency, where the intervals between each pulse in a train can be varied.

FIG. 2A illustrates an exemplary electrical voltage/current profile for a stimulating, blocking and/or modulating impulse applied to a portion or portions of selected nerves in accordance with an embodiment of the present invention. For the preferred embodiment, the voltage and current refer to those that are non-invasively produced within the patient by the electrodes (or magnetic coils). As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the electrodes 340 that deliver the stimulating, blocking and/or modulating impulse 410 to the nerve. Nerve stimulating/modulating device 302 may be externally powered and/or recharged or may have its own power source 320. The parameters of the modulation signal 400, such as the frequency, amplitude, duty cycle, pulse width, pulse shape, etc., are preferably programmable. An external communication device may modify the pulse generator programming to improve treatment.

In addition, or as an alternative to the devices to implement the modulation unit for producing the electrical voltage/current profile of the stimulating, blocking and/or modulating impulse to the electrodes, the device disclosed in patent publication No. US2005/0216062 may be employed. That patent publication discloses a multifunctional electrical stimulation (ES) system adapted to yield output signals for effecting electromagnetic or other forms of electrical stimulation for a broad spectrum of different biological and biomedical applications, which produce an electric field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated, as well as the outputs of various sensors which sense prevailing conditions prevailing in this substance, whereby the user of the system can manually adjust the signal, or have it automatically adjusted by feedback, to provide an electrical stimulation signal of whatever type the user wishes, who can then observe the effect of this signal on a substance being treated.

The stimulating and/or modulating impulse signal 410 preferably has a frequency, an amplitude, a duty cycle, a pulse width, a pulse shape, etc. selected to influence the therapeutic result, namely, stimulating and/or modulating some or all of the transmission of the selected nerve. For example, the frequency may be about 1 Hz or greater, such as between about 15 Hz to 100 Hz, preferably between about 15-50 Hz and more preferably between about 15-35 Hz. In an exemplary embodiment, the frequency is 25 Hz. The modulation signal may have a pulse width selected to influence the therapeutic result, such as about 1 microseconds to about 1000 microseconds, preferably about 100-400 microseconds and more preferably about 200-400 microseconds. For example, the electric field induced or produced by the device within tissue in the vicinity of a nerve may be about 5 to 600 V/m, preferably less than 100 V/m, and even more preferably less than 30 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz. The modulation signal may have a peak voltage amplitude selected to influence the therapeutic result, such as about 0.2 volts or greater, such as about 0.2 volts to about 40 volts, preferably between about 1-20 volts and more preferably between about 2-12 volts.

An objective of some of the disclosed stimulators is to provide both nerve fiber selectivity and spatial selectivity. Spatial selectivity may be achieved in part through the design of the electrode (or magnetic coil) configuration, and nerve fiber selectivity may be achieved in part through the design of the stimulus waveform, but designs for the two types of selectivity are intertwined. This is because, for example, a waveform may selectively stimulate only one of two nerves whether they lie close to one another or not, obviating the need to focus the stimulating signal onto only one of the nerves [GRILL W and Mortimer J T. Stimulus waveforms for selective neural stimulation. IEEE Eng. Med. Biol. 14 (1995): 375-385]. These methods complement others that are used to achieve selective nerve stimulation, such as the use of local anesthetic, application of pressure, inducement of ischemia, cooling, use of ultrasound, graded increases in stimulus intensity, exploiting the absolute refractory period of axons, and the application of stimulus blocks [John E. SWETT and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-295].

To date, the selection of stimulation waveform parameters for nerve stimulation has been highly empirical, in which the parameters are varied about some initially successful set of parameters, in an effort to find an improved set of parameters for each patient. A more efficient approach to selecting stimulation parameters might be to select a stimulation waveform that mimics electrical activity in the anatomical regions that one is attempting stimulate indirectly, in an effort to entrain the naturally occurring electrical waveform, as suggested in patent number U.S. Pat. No. 6,234,953, entitled Electrotherapy device using low frequency magnetic pulses, to THOMAS et al. and application number US20090299435, entitled Systems and methods for enhancing or affecting neural stimulation efficiency and/or efficacy, to GLINER et al. One may also vary stimulation parameters iteratively, in search of an optimal setting [U.S. Pat. No. 7,869,885, entitled Threshold optimization for tissue stimulation therapy, to BEGNAUD et al]. However, some stimulation waveforms, such as those described herein, are discovered by trial and error, and then deliberately improved upon.

Invasive nerve stimulation typically uses square wave pulse signals. However, Applicant found that square waveforms are not ideal for non-invasive stimulation as they produce excessive pain. Prepulses and similar waveform modifications have been suggested as methods to improve selectivity of nerve stimulation waveforms, but Applicant did not find them ideal [Aleksandra VUCKOVIC, Marco Tosato and Johannes J Struijk. A comparative study of three techniques for diameter selective fiber activation in the vagal nerve: anodal block, depolarizing prepulses and slowly rising pulses. J. Neural Eng. 5 (2008): 275-286; Aleksandra VUCKOVIC, Nico J. M. Rijkhoff, and Johannes J. Struijk. Different Pulse Shapes to Obtain Small Fiber Selective Activation by Anodal Blocking—A Simulation Study. IEEE Transactions on Biomedical Engineering 51 (5, 2004): 698-706; Kristian HENNINGS. Selective Electrical Stimulation of Peripheral Nerve Fibers: Accommodation Based Methods. Ph.D. Thesis, Center for Sensory-Motor Interaction, Aalborg University, Aalborg, Denmark, 2004].

Figure 2B:
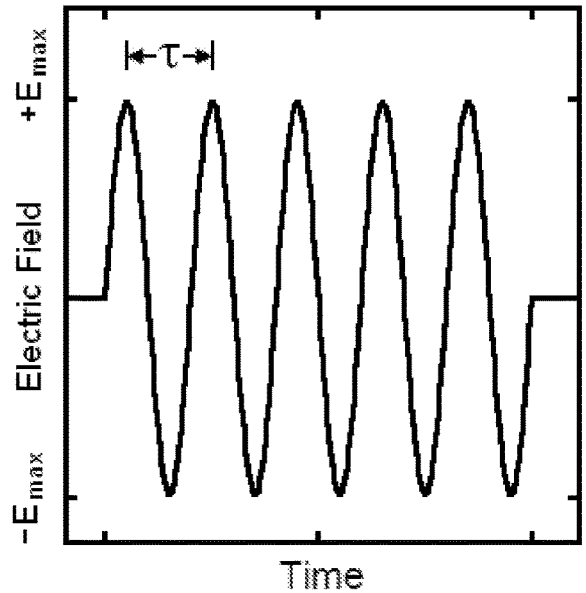
FIG. 2B illustrates an exemplary bursting electrical waveform for stimulating and/or modulating a nerve according to the present invention.
Figure 2C:
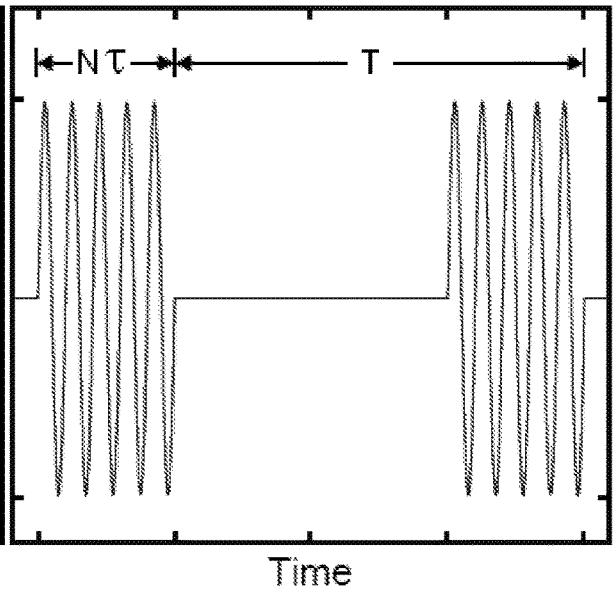
FIG. 2C illustrates two successive bursts of the waveform of FIG. 2B.

Applicant also found that stimulation waveforms consisting of bursts of square pulses are not ideal for non-invasive stimulation [M. I. JOHNSON, C. H. Ashton, D. R. Bousfield and J. W. Thompson. Analgesic effects of different pulse patterns of transcutaneous electrical nerve stimulation on cold-induced pain in normal subjects. Journal of Psychosomatic Research 35 (2/3, 1991): 313-321; U.S. Pat. No. 7,734,340, entitled Stimulation design for neuromodulation, to De Ridder]. However, bursts of sinusoidal pulses are a preferred stimulation waveform, as shown in FIGS. 2B and 2C. As seen there, individual sinusoidal pulses have a period of and a burst consists of N such pulses. This is followed by a period with no signal (the inter-burst period). The pattern of a burst followed by silent inter-burst period repeats itself with a period of T. For example, the sinusoidal period τ may be between about 50-1000 microseconds (equivalent to about 1-20 KHz), preferably between about 100-400 microseconds (equivalent to about 2.5-10 KHz), more preferably about 133-400 microseconds (equivalent to about 2.5-7.5 KHZ) and even more preferably about 200 microseconds (equivalent to about 5 KHz); the number of pulses per burst may be N=1-20, preferably about 2-10 and more preferably about 5; and the whole pattern of burst followed by silent inter-burst period may have a period T comparable to about 10-100 Hz, preferably about 15-50 Hz, more preferably about 25-35 Hz and even more preferably about 25 Hz (a much smaller value of T is shown in FIG. 2E to make the bursts discernable). When these exemplary values are used for T and τ the waveform contains significant Fourier components at higher frequencies (1/200 microseconds=5000/sec), as compared with those contained in transcutaneous nerve stimulation waveforms, as currently practiced.

The above waveform is essentially a 1-20 KHz signal that includes bursts of pulses with each burst having a frequency of about 10-100 Hz and each pulse having a frequency of about 1-20 KHz. Another way of thinking about the waveform is that it is a 1-20 KHz waveform that repeats itself at a frequency of about 10-100 Hz. Applicant is unaware of such a waveform having been used with stimulation of a branch of the trigeminal nerve, but a similar waveform has been used to stimulate muscle as a means of increasing muscle strength in elite athletes. However, for the muscle strengthening application, the currents used (200 mA) may be very painful and two orders of magnitude larger than what are disclosed herein. Furthermore, the signal used for muscle strengthening may be other than sinusoidal (e.g., triangular), and the parameters τ, N, and T may also be dissimilar from the values exemplified above [A. DELITTO, M. Brown, M. J. Strube, S. J. Rose, and R. C. Lehman. Electrical stimulation of the quadriceps femoris in an elite weight lifter: a single subject experiment. Int J Sports Med 10(1989):187-191; Alex R WARD, Nataliya Shkuratova. Russian Electrical Stimulation: The Early Experiments. Physical Therapy 82 (10, 2002): 1019-1030; Yocheved LAUFER and Michal Elboim. Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88 (10, 2008): 1167-1176; Alex R WARD. Electrical Stimulation Using Kilohertz-Frequency Alternating Current. Physical Therapy 89 (2, 2009): 181-190; J. PETROFSKY, M. Laymon, M. Prowse, S. Gunda, and J. Batt. The transfer of current through skin and muscle during electrical stimulation with sine, square, Russian and interferential waveforms. Journal of Medical Engineering and Technology 33 (2, 2009): 170-181; U.S. Pat. No. 4,177,819, entitled Muscle stimulating apparatus, to KOFSKY et al]. Burst stimulation has also been disclosed in connection with implantable pulse generators, but wherein the bursting is characteristic of the neuronal firing pattern itself [U.S. Pat. No. 7,734,340 to DE RIDDER, entitled Stimulation design for neuromodulation; application US20110184486 to DE RIDDER, entitled Combination of tonic and burst stimulations to treat neurological disorders]. By way of example, the electric field shown in FIGS. 2B and 2C may have an $E_{max}$ value of 17 V/m, which is sufficient to stimulate the nerve but is significantly lower than the threshold needed to stimulate surrounding muscle.

High frequency electrical stimulation is also known in the treatment of back pain at the spine [patent application US20120197369, entitled Selective high frequency spinal cord modulation for inhibiting pain with reduced side effects and associated systems and methods, to ALATARIS et al.; Adrian A L KAISY, Iris Smet, and Jean-Pierre Van Buyten. Analgeia of axial low back pain with novel spinal neuromodulation. Poster presentation #202 at the 2011 meeting of The American Academy of Pain Medicine, held in National Harbor, Md., Mar. 24-27, 2011].

Those methods involve high-frequency modulation in the range of from about 1.5 KHz to about 50 KHz, which is applied to the patient's spinal cord region. However, such methods are different from the present invention because, for example, they are invasive; they do not involve a bursting waveform, as in the present invention; they necessarily involve A-delta and C nerve fibers and the pain that those fibers produce, whereas the present invention does not; they may involve a conduction block applied at the dorsal root level, whereas the present invention may stimulate action potentials without blocking of such action potentials; and/or they involve an increased ability of high frequency modulation to penetrate through the cerebral spinal fluid, which is not relevant to the present invention. In fact, a likely explanation for the reduced back pain that is produced by their use of frequencies from 10 to 50 KHz is that the applied electrical stimulus at those frequencies causes permanent damage to the pain-causing nerves, whereas the present invention involves only reversible effects [LEE R C, Zhang D, Hannig J. Biophysical injury mechanisms in electrical shock trauma. Annu Rev Biomed Eng 2(2000):477-509].

Consider now which nerve fibers may be stimulated by the non-invasive nerve stimulation. A branch of the trigeminal nerve in man consists of thousands of nerve fibers (axons), mostly organized into groups. The groups are contained within fascicles of varying sizes, which branch and converge along the nerve. Under normal physiological conditions, each fiber conducts electrical impulses only in one direction, which is defined to be the orthodromic direction, and which is opposite the antidromic direction. However, external electrical stimulation of the nerve may produce action potentials that propagate in orthodromic and antidromic directions. Besides efferent output fibers that convey signals to the body from the central nervous system, the nerve conveys sensory (afferent) information about the state of the body's organs back to the central nervous system.

The largest nerve fibers within a trigeminal nerve branch are approximately 20 μm in diameter and are heavily myelinated, whereas only the smallest nerve fibers of less than about 1 μm in diameter are completely unmyelinated. When the distal part of a nerve is electrically stimulated, an electrode located more proximally may record a compound action potential. A compound action potential contains several peaks or waves of activity that represent the summated response of multiple fibers having similar conduction velocities. The waves in a compound action potential represent different types of nerve fibers that are classified into corresponding functional categories, with approximate diameters as follows: A-alpha fibers (afferent or efferent fibers, 12-20

μm diameter), A-beta fibers (afferent or efferent fibers, 5-12 μm), A-gamma fibers (efferent fibers, 3-7 μm), A-delta fibers (afferent fibers, 2-5 μm), B fibers (1-3 μm) and C fibers (unmyelinated, 0.4-1.2 μm). The diameters of group A and group B fibers include the thickness of the myelin sheaths [CRUCCU G, Pennisi E, Truini A, Iannetti G D, Romaniello A, Le Pera D, De Armas L, Leandri M, Manfredi M, Valeriani M. Unmyelinated trigeminal pathways as assessed by laser stimuli in humans. Brain 126 (Pt 10, 2003): 2246-2256].

The waveform disclosed in FIG. 2 contains significant Fourier components at high frequencies (e.g., 1/200 microseconds=5000/sec), even if the waveform also has components at lower frequencies (e.g., 25/sec). Transcutaneously, A-beta, A-delta, and C fibers are typically excited at 2000 Hz, 250 Hz, and 5 Hz, respectively, i.e., the 2000 Hz stimulus is described as being specific for measuring the response of A-beta fibers, the 250 Hz for A-delta fibers, and the 5 Hz for type C fibers [George D. BAQUIS et al. TECHNOLOGY REVIEW: THE NEUROMETER CURRENT PERCEPTION THRESHOLD (CPT). Muscle Nerve 22 (Supplement 8, 1999): S247-S259]. Therefore, the high frequency component of the noninvasive stimulation waveform will preferentially stimulate the A-alpha and A-beta fibers, and the C fibers will be largely unstimulated.

However, the threshold for activation of fiber types also depends on the amplitude of the stimulation, and for a given stimulation frequency, the threshold increases as the fiber size decreases. The threshold for generating an action potential in nerve fibers that are impaled with electrodes is traditionally described by Lapicque or Weiss equations, which describe how together the width and amplitude of stimulus pulses determine the threshold, along with parameters that characterize the fiber (the chronaxy and rheobase). For nerve fibers that are stimulated by electric fields that are applied externally to the fiber, as is the case here, characterizing the threshold as a function of pulse amplitude and frequency is more complicated, which ordinarily involves the numerical solution of model differential equations or a case-by-case experimental evaluation [David BOINAGROV, Jim Loudin and Daniel Palanker. Strength-Duration Relationship for Extracellular Neural Stimulation: Numerical and Analytical Models. J Neurophysiol 104(2010):2236-2248].

For example, REILLY describes a model (the spatially extended nonlinear nodal model or SENN model) that may be used to calculate minimum stimulus thresholds for nerve fibers having different diameters [J. Patrick REILLY. Electrical models for neural excitation studies. Johns Hopkins APL Technical Digest 9 (1, 1988): 44-59]. According to REILLY's analysis, the minimum threshold for excitation of myelinated A fibers is 6.2 V/m for a 20 □m diameter fiber, 12.3 V/m for a 10 □m fiber, and 24.6 V/m for a 5 □m diameter fiber, assuming a pulse width that is within the contemplated range of the present invention (1 ms). It is understood that these thresholds may differ slightly from those produced by the waveform of the present invention as illustrated by REILLY's figures, for example, because the present invention prefers to use sinusoidal rather than square pulses. Thresholds for B and C fibers are respectively 2 to 3 and 10 to 100 times greater than those for A fibers [Mark A. CASTORO, Paul B. Yoo, Juan G. Hincapie, Jason J. Hamann, Stephen B. Ruble, Patrick D. Wolf, Warren M. Grill. Excitation properties of the right cervical vagus nerve in adult dogs. Experimental Neurology 227 (2011): 62-68]. If we assume an average A fiber threshold of 15 V/m, then B fibers would have thresholds of 30 to 45 V/m and C fibers would have thresholds of 150 to 1500 V/m. The present invention produces electric fields at the nerve in the range of about 6 to 100 V/m, which is therefore generally sufficient to excite all myelinated A and B fibers, but not the unmyelinated C fibers. In contrast, invasive nerve stimulators that have been used for the treatment of epilepsy have been reported to excite C fibers in some patients [EVANS M S, Verma-Ahuja S, Naritoku D K, Espinosa J A. Intraoperative human vagus nerve compound action potentials. Acta Neurol Scand 110(2004): 232-238].

It is understood that although devices of the present invention may stimulate A and B nerve fibers, in practice they may also be used so as not to stimulate the largest A fibers (A-delta) and B fibers. In particular, if the stimulator amplitude has been increased to the point at which unwanted side effects begin to occur, the operator of the device may simply reduce the amplitude to avoid those effects. Because stimulation with the disclosed devices does not produce nociceptive effects that would be produced by A-delta fibers or C fibers, evidently the A-delta fibers may not be stimulated when the amplitude is properly set.

Figure 11:
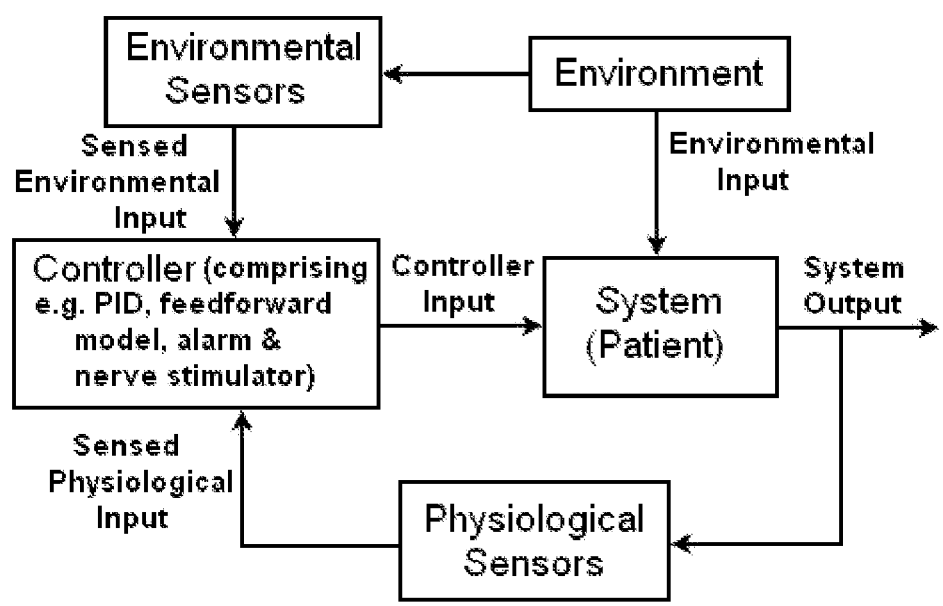
FIG. 11 illustrates connections between the controller and controlled system according to the present invention, their input and output signals, and external signals from the environment.

The use of feedback to generate the modulation signal 400 may result in a signal that is not periodic, particularly if the feedback is produced from sensors that measure naturally occurring, time-varying aperiodic physiological signals from the patient (see FIG. 11). In fact, the absence of significant fluctuation in naturally occurring physiological signals from a patient is ordinarily considered to be an indication that the patient is in ill health. This is because a pathological control system that regulates the patient's physiological variables may have become trapped around only one of two or more possible steady states and is therefore unable to respond normally to external and internal stresses. Accordingly, even if feedback is not used to generate the modulation signal 400, it may be useful to artificially modulate the signal in an aperiodic fashion, in such a way as to simulate fluctuations that would occur naturally in a healthy individual. Thus, the noisy modulation of the stimulation signal may cause a pathological physiological control system to be reset or undergo a non-linear phase transition, through a mechanism known as stochastic resonance [B. SUKI, A. Alencar, M. K. Sujeer, K. R. Lutchen, J. J. Collins, J. S. Andrade, E. P. Ingenito, S. Zapperi, H. E. Stanley, Life-support system benefits from noise, Nature 393 (1998) 127-128; W Alan C MUTCH, M Ruth Graham, Linda G Girling and John F Brewster. Fractal ventilation enhances respiratory sinus arrhythmia. Respiratory Research 2005, 6:41, pp. 1-9].

So, in one embodiment of the present invention, the modulation signal 400, with or without feedback, will stimulate the selected nerve fibers in such a way that one or more of the stimulation parameters (power, frequency, and others mentioned herein) are varied by sampling a statistical distribution having a mean corresponding to a selected, or to a most recent running-averaged value of the parameter, and then setting the value of the parameter to the randomly sampled value. The sampled statistical distributions will comprise Gaussian and 1/f, obtained from recorded naturally occurring random time series or by calculated formula. Parameter values will be so changed periodically, or at time intervals that are themselves selected randomly by sampling another statistical distribution, having a selected mean and coefficient of variation, where the sampled distributions comprise Gaussian and exponential, obtained from recorded naturally occurring random time series or by calculated formula.

In another embodiment, devices in accordance with the present invention are provided in a "pacemaker" type form, in which electrical impulses 410 are generated to a selected region of the nerve by a stimulator device on an intermittent basis, to create in the patient a lower reactivity of the nerve.

Preferred Embodiments of the Electrode-Based Stimulator

The electrodes of the invention are applied to the skin surface of the head, or to some other surface of the body, and are used to deliver electrical energy non-invasively to a nerve. Embodiments of the present invention may differ with regard to the number of electrodes that are used, the distance between electrodes, and whether disk or ring electrodes are used. In preferred embodiments of the method, one selects the electrode configuration for individual patients, in such a way as to optimally focus electric fields and currents onto the selected nerve, without generating excessive currents on the surface of the skin. This tradeoff between focality and surface currents is described by DATTA et al. [Abhishek DATTA, Maged Elwassif, Fortunato Battaglia and Marom Bikson. Transcranial current stimulation focality using disc and ring electrode configurations: FEM analysis. J. Neural Eng. 5 (2008): 163-174]. Although DATTA et al. are addressing the selection of electrode configuration specifically for transcranial current stimulation, the principles that they describe are applicable to peripheral nerves as well [RATTAY F. Analysis of models for extracellular fiber stimulation. IEEE Trans. Biomed. Eng. 36 (1989): 676-682].

A preferred embodiment of an electrode-based stimulator is shown in FIG. 3. As shown, the stimulator comprises a smartphone (31) with its back cover removed and joined to a housing (32) that comprises a pair of electrode surfaces (33) along with circuitry (not shown) to control and power the electrodes and interconnect with the smartphone. The electrode surface (33) in FIG. 3 corresponds to item 351 in FIG. 1. FIG. 3A shows the side of the smartphone (31) with a touch-screen. FIG. 3B shows the housing of the stimulator (32) joined to the back of the smartphone. Portions of the housing lie flush with the back of the smartphone, with windows to accommodate smartphone components that are found on the original back of the smartphone. Such components may also be used with the stimulator, e.g., the smartphone's rear camera (34), flash (35) and speaker (36). Other original components of the smartphone may also be used, such as the audio headset jack socket (37) and multi-purpose jack (38). Note that the original components of the smartphone shown in FIG. 3 correspond to a Samsung Galaxy smartphone, and their locations may be different for embodiments that use different smartphone models.

FIG. 3C shows that several portions of the housing (32) protrude towards the back. The two electrode surfaces (33) protrude so that they may be applied to the skin of the patient. The stimulator may be held in place by straps or frames or collars, or the stimulator may be held against the patient's body by hand. Other embodiments of the invention may comprise a single such electrode surface or more than two electrode surfaces.

A dome (39) also protrudes from the housing, so as to allow the device to lie more or less flat on a table when supported also by the electrode surfaces. The dome also accommodates a relatively tall component that may lie underneath it, such as a battery. If the battery under the dome is rechargeable, the dome may contain a socket (41) through which the battery is recharged using a jack that is inserted into it, which is, for example, attached to a power cable from a base station (described below). The belly (40) of the housing protrudes to a lesser extent than the electrodes and dome. The belly accommodates a printed circuit board that contains electronic components within the housing (not shown), as described below.

Generally, the stimulator is designed to situate the electrodes of the stimulator (340 in FIG. 1) remotely from the surface of the skin within a chamber, with conducting material (350 in FIG. 1) placed in a chamber between the electrode and the exterior component of the stimulator head that contacts the skin (351 in FIG. 1). One of the novelties of this design is that the stimulator, along with a correspondingly suitable stimulation waveform (see FIG. 2), shapes the electric field, producing a selective physiological response by stimulating that nerve, but avoiding substantial stimulation of nerves and tissue other than the target nerve, particularly avoiding the stimulation of nerves that produce pain. The shaping of the electric field is described in terms of the corresponding field equations in co-pending, commonly assigned application US20110230938 (application Ser. No. 13/075,746), entitled Devices and methods for non-invasive electrical stimulation and their use for vagal nerve stimulation on the neck of a patient, to SIMON et al., which is hereby incorporated by reference.

In certain embodiments, the disc interface 351 actually functions as the electrode and the screw 340 is simply the output connection to the signal generator electronics. In this embodiment, electrically conductive fluid or gel is positioned between the signal generator and the interface or electrode 351. In this embodiment, the conductive fluid filters out or eliminates high frequency components from the signal to smooth out the signal before it reaches the electrode(s) 351. When the signal is generated, power switching and electrical noise typically add unwanted high frequency spikes back into the signal. In addition, the pulsing of the sinusoidal bursts may induce high frequency components in the signal. By filtering the signal just before it reaches the electrodes 351 with the conductive fluid, a smoother, cleaner signal is applied to the patient, thereby reducing the pain and discomfort felt by the patient and allowing a higher amplitude to be applied to the patient. This allows a sufficiently strong signal to be applied to reach a deeper nerve, such as the vagus nerve, without causing too much pain and discomfort to the patient at the surface of their skin.

In other embodiments, a low-pass filter may be used instead of the electrically conductive fluid to filter out the undesirable high frequency components of the signal. The low-pass filter may comprise a digital or active filter or simply two series resistors and a parallel capacitor placed between the signal generator and the electrode/interface.

Figure 4A:
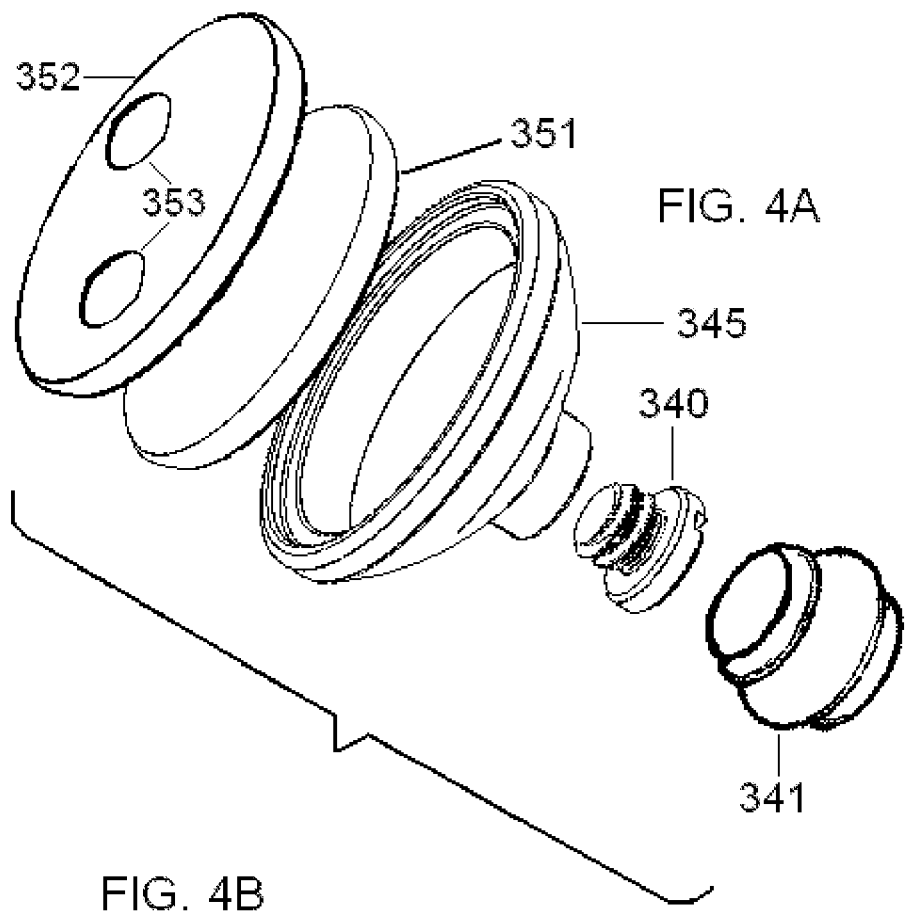
FIG. 4A illustrates an exploded view of an electrode assembly according to one embodiment of the present invention.
Figure 4B:
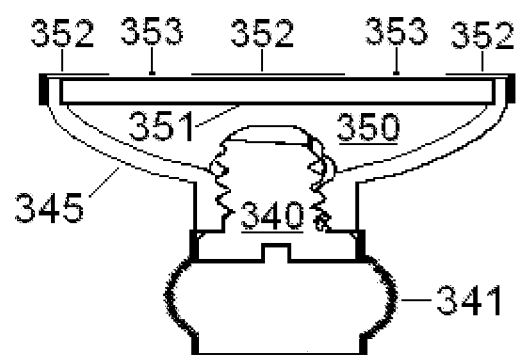
FIG. 4B illustrates an assembled view of the electrode assembly shown in FIG. 4A.

The electrode surface (33) was shown in FIG. 3C as being roughly hemispherical so that as the electrode surface is pressed into the patient's skin, the surface area of skin contact would increase. However, in other designs of the electrode surface (corresponding to 351 in FIG. 1), the electrode surface may be flat. Such an alternate design is shown in FIG. 4. As shown in FIG. 4A, the electrode surface (351) comprises a metal (e.g., stainless steel) disc that fits into the top of a non-conducting (e.g., plastic) chamber (345). At the other end of the chamber, a threaded port accepts a metal screw that serves as the actual electrode (340). A wire will be attached to the screw, connecting it to impulse generating circuitry. The assembled components are shown in FIG. 4B, which also shows the location of an electrically conducting material (350) within the chamber, such as an electrolyte solution or gel, that allows the electrode (340) to conduct current to the external electrode surface (351).

In some of the present applications, that alternate electrode design is modified in two ways. First, the electrode is made flexible so that it can adapt to placement against skin surfaces that are not entirely planar. Furthermore, even if the surfaces are planar, the planes against which two or more electrodes are applied need not the same. For example, to accommodate curvature of the skin surface, the outer electrode surface (351) may be made of a conductive elastomer, such as Metal Rubber (NanoSonic, Inc., 158 Wheatland Drive, Wheatland EcoPark Pembroke, Va. USA 24136), and the non-conducting chamber (345) may likewise be made of rubber-like polymers. Furthermore, by mounting the electrode on a flexible (e.g., rubber tubing) joint (341), the electrode may also be allowed to pivot relative to its relaxed central axis, in order to press against a skin surface that is initially not flush with the electrode surface.

The second modification of the alternate electrode design is to mask portions of the electrode surface (351) in such a way as to achieve high current density at only one or more particular locations on the surface of the skin. This is done by cutting holes (353) in a thin non-conducting cap (352) that is placed over the electrode surface (351). If desired, an electrically conducting gel may also be placed onto the electrode surface (351) at the locations of the holes (353) to improve the electrical contact of the electrode surface with the skin at the holes, although this may generally not be necessary if the non-conducting cap (352) is thin. As shown in FIG. 4A, there are two holes, which in the present application could correspond to precise, individualized locations of the supraorbital nerve and the supratrochlear nerve near the orbit of the patient's eye (see below). The patient may also position the stimulator in different orientations, and in some of them, different caps may be used, or no cap may be used, for one or both electrodes (see FIG. 10).

Electronics and Software of the Stimulator

In one embodiment, the signal waveform (FIG. 2) that is to be applied to electrodes of the stimulator is initially generated in a component of the impulse generator (310 in FIG. 1) that is exterior to, and remote from, the mobile phone housing. The mobile phone preferably includes a software application that can be downloaded into the phone to receive, from the external control component, a wirelessly transmitted waveform, or to receive a waveform that is transmitted by cable, e.g., via the multi-purpose jack 38 in FIG. 3. If the waveforms are transmitted in compressed form, they are preferably compressed in a lossless manner, e.g., making use of FLAC (Free Lossless Audio Codec). Alternatively, the downloaded software application may itself be coded to generate a particular waveform that is to be applied to the electrodes (340 in FIG. 1) and subsequently conveyed to the external interface of the electrode assembly (351 in FIGS. 1 and 33 in FIG. 3). In yet another embodiment, the software application is not downloaded from outside the device, but is instead available internally, for example, within read-only-memory that is present within the housing of the stimulator (32 in FIGS. 3B and 3C).

In one embodiment, the waveform is first conveyed by the software application to contacts within the phone's earphone jack socket (37 in FIG. 3B), as though the waveform signal were a generic audio waveform. That pseudo-audio waveform will generally be a stereo waveform, representing signals that are to be applied to the "left" and "right" electrodes. The waveform will then be conveyed to the housing of the stimulator (32 in FIGS. 3B and 3C), as follows. The housing of the stimulator may have an attached dangling audio jack that is plugged into earphone jack socket 37 whenever electrical stimulation is to be performed, or the electrical connection between the contacts of the earphone jack socket and the housing of the stimulator may be hard-wired. In either case, electrical circuits on a printed circuit board located under the belly of the housing (40 in FIG. 3C) of the stimulator may then shape, filter, and/or amplify the pseudo-audio signal that is received via the earphone jack socket. A power amplifier within the housing of the stimulator may then drive the signal onto the electrodes, in a fashion that is analogous to the use of an audio power amplifier to drive loudspeakers. Alternatively, the signal processing and amplification may be implemented in a separate device that can be plugged into sockets on the phone and/or housing of the stimulator (32 in FIGS. 3B and 3C), to couple the software application and the electrodes.

In addition to passing the stimulation waveform from the smartphone to the stimulator housing as described above, the smartphone may also pass control signals to the stimulator housing. Thus, the stimulation waveform may generally be regarded as a type of analog, pseudo-audio signal, but if the signal contains a signature series of pulses signifying that a digital control signal is about to be sent, logic circuitry in the stimulator housing may then be set to decode the series of digital pulses that follows the signature series of pulses, analogous to the operation of a modem.

Many of the steps that direct the waveform to the electrodes, including steps that may be controlled by the user via the touchscreen (31 in FIG. 3A), are implemented in the above-mentioned software application. By way of example, the software application may be written for a phone that uses the Android operating system. Such applications are typically developed in the Java programming language using the Android Software Development Kit (SDK), in an integrated development environment (IDE), such as Eclipse [Mike WOLFSON. Android Developer Tools Essentials. Sebastopol, Calif.: O'Reilly Media Inc., 2013; Ronan SCHWARZ, Phil Duston, James Steele, and Nelson To. The Android Developer's Cookbook. Building Applications with the Android SDK, Second Edition. Upper Saddle River, N J: Addison-Wesley, 2013; Shane CONDER and Lauren Darcey. Android Wireless Application Development, Second Edition. Upper Saddle River, N.J.: Addison-Wesley, 2011; Jerome F. DIMARZIO. Android—A Programmer's Guide. New York: McGraw-Hill. 2008. pp. 1-319]. Application programming interfaces (APIs) that are particularly relevant to the audio features of such an Android software application (e.g., MediaPlayer APIs) are described by: Android Open Source Project of the Open Handset Alliance. Media Playback, at web domain developer.android.com with subdomain/guide/topics/media/, Jul. 18, 2014. Those APIs are also particularly relevant to the invention's use of the smartphone camera capabilities, as described below. Additional components of the software application are available from device manufacturers [Samsung Mobile SDK, at web domain developer.samsung.com with subdomain/samsung-mobile-sdk, Jul. 18, 2014].

In certain embodiments, the stimulator and/or smartphone will include a user control, such as a switch or button, that disables/enables the stimulator. Preferably, the switch will automatically disable all smartphone functions when the stimulator is enabled (and vice versa). This ensures that the medical device functionality of the smartphone is completely segregated from the rest of the phone's functionality. In preferred embodiments, the switch will be password-controlled such that only the patient/owner of the stimulator/phone will be able to enable the stimulator functionality. In one such embodiment, the switch will be controlled by a biometric scan (e.g., fingerprint, optical scan or the like)

such that the stimulator functionality can only be used by the patient. This ensures that only the patient will be able to use the prescribed therapy in the event the phone is lost or stolen.

The stimulator and/or phone will also include software that allows the patient to order more therapy doses over the internet (discussed in more detail below in connection with the docking station). The purchase of such therapy doses will entail physician authorization through a prescription or the like. To that end, the software will preferably include an authorization code that should be entered in order for the patient to download authorization for more therapies. Without such authorization, the stimulator will be disabled and will not deliver therapy.

Although the device shown in FIG. 3 is an adapted commercially available smartphone, it is understood that in some embodiments, the housing of the stimulator may also be joined to and/or powered by a wireless device that is not a phone (e.g., Wi-Fi enabled device). Alternatively, the stimulator may be coupled to a phone or other Wi-Fi enabled device through a wireless connection for exchanging data at short distances, such as Bluetooth or the like. In this embodiment, the stimulator housing is not attached to the smartphone and, therefore, may comprise a variety of other shapes and sizes that are convenient for the patient to carry in his or her purse, wallet or pocket.

In other embodiments, the stimulator housing may be designed as part of a protective or decorative case for the phone that can be attached to the phone, similar to standard phone cases. In one such embodiment, the stimulator/case may also include additional battery life for the phone and may include an electrical connection to the phone's battery to recharge the battery (e.g., part of a Mophie® or the like). This electrical connection may also be used to couple the smartphone to the stimulator.

Use of the Smartphone's Rear Camera to Position the Electrodes

Reproducibility of the effects of electrical stimulation of a selected nerve depends in part on one's ability to position the electrode surfaces to an optimal location on the patient's skin during successive stimulation sessions. The present invention includes methods for repositioning the stimulation device during subsequent sessions. The methods that are disclosed below involve initially determining an optimal position for the stimulator by imaging the nerve with ultrasound, then marking that position on the patient's skin with spots of dyes ("tattoos"), and eventually repositioning the stimulation device in conjunction with imaging the spots of dyes with the rear camera of the smartphone.

The preferred ultrasound transducer/probe used to image the stimulated nerve is a "hockey stick" style of probe, so-called because of its shape, which is commercially available from most ultrasound machine manufacturers. As an example, the Hitachi Aloka UST-536 19 mm Hockey Stick style Transducer for superficial viewing has a frequency range of 6-13 MHz, a scan angle of 90 degrees, and a probe surface area of approximately 19 mm×4 mm (Hitachi Aloka Medical America, 10 Fairfield Boulevard, Wallingford Conn. 06492). The transducer connects to the ultrasound machine that displays the anatomical structures that lie under the transducer.

The location for electrically stimulating a branch of the trigeminal (or other) nerve is determined preliminarily by positioning an ultrasound probe at the location where the center of each smartphone electrode will be placed (33 in FIG. 3), such that the nerve appears in the center of the ultrasound image [Michael SEIN and Imanuel Lerman. Peripheral nerve stimulator placement with ultrasound guidance for the treatment of intractable postherpetic neuralgia: A case report. Poster 267. Proceedings of the 17th Annual Meeting of the North American Neuromodulation Society. Dec. 5-8, 2013, Las Vegas, Nev., USA. page 1; SPINNER D, Kirschner J S. Accuracy of ultrasound-guided superficial trigeminal nerve blocks using methylene blue in cadavers. Pain Med 13 (11, 2012): 1469-1473]. Once that location has been found for an electrode, temporary spots are marked on the patient's skin with ink to preserve knowledge of the location and orientation of the ultrasound probe, through stencil holes that are attached on both sides of the shorter dimension of the ultrasound probe. When the preferred ultrasound location on the skin for each electrode has been ascertained, the interpolated optimal location under the center of the rear camera is then marked (tattooed) on the patient's skin with one of the more permanent fluorescent dyes that are described below. The interpolation may be performed using a long, rectangular stencil with several holes, wherein holes near the ends of the stencil are aligned with the temporary spots that had been marked for the electrode locations, and wherein a central hole of the stencil is used to apply the permanent fluorescent dye to a location that will lie under the smartphone camera. Ordinarily two or more adjacent fluorescent dye locations are marked, such that if the stencil is subsequently aligned centrally over the fluorescent spots on the skin, the end holes of the stencil would also align with the temporary spot locations that had been marked to record the ultrasound probe location matching electrode locations.

It is understood that any non-toxic dye may be used to permanently mark a location on the patient's skin. However, the preferred type of permanent dye is a fluorophore that is only visible or detectable as a spot on the patient's head when one shines non-visible light upon it, e.g., ultraviolet light ("blacklight") or infrared light. This is because the patient is thereby spared the embarrassment of explaining why there would otherwise be a visible spot mark on his or her head, and also because such a dye is suitable for showing where to place the stimulator irrespective of whether the patient is dark-skinned or light-skinned. Another method, which is to attempt to match the color of the dye to the patient's flesh color, would be generally impractical. Marking with a fluorescent dye (e.g., from ordinary highlighting pens) has been performed previously by surgeons and radiologists to outline where a procedure is to be performed. However, the marking in the present invention is different in that it is intended to be used repeatedly by a patient alone for device positioning at small discrete spots [DAVID, J. E., Castle, S. K. B., and Mossi, K. M. Localization tattoos: an alternative method using fluorescent inks. Radiation Therapist 15(2006):1-5; WATANABE M, Tsunoda A, Narita K, Kusano M, Miwa M. Colonic tattooing using fluorescence imaging with light-emitting diode-activated indocyanine green: a feasibility study. Surg Today 39 (3, 2009): 214-218].

Once the position-indicating fluorescent spots have been applied on the patient's skin as described above, they may fade and eventually disappear as the stained outer surface of the patient's skin exfoliates. The exfoliation will occur naturally as the patient washes his or her head and may be accelerated by mechanical (e.g., abrasive) or chemical methods that are routinely used by cosmetologists. Before the spot disappears, the patient or a family member may reapply the dye/fluorophor to the same spot while observing it with ultraviolet or infrared light (as the case may be), by masking the skin outside the spot and then applying new dye solution directly with a cotton swab. Viewing of the fluorescence that is excited by ultraviolet light can be done with the naked eye because it comprises blue light, and viewing of fluorescence that is excited by infrared light can be done with a conventional digital camera after removing the camera's IR-blocking filter. For some cameras, removal of an IR-blocking filter may not be necessary (e.g., those that can perform retinal biometric scans). Some of the infrared fluorescent dyes may also be faintly visible to the naked eye even under room light, depending on their concentration (e.g., indocyanine green).

Alternatively, a semi-permanent or permanent tattooing method of marking or re-marking the fluorescent spots may be used by a licensed professional tattooer, by injecting the dye/fluorophor into an outer skin layer or deeper into the skin [Maria Luisa Perez-COTAPOS, Christa De Cuyper, and Laura Cossio. Tattooing and scarring: techniques and complications. In: Christa de Cuyper and Maria Luisa Cotapos (Eds.). Dermatologic Complications with Body Art: Tattoos, Piercings and Permanent Make-Up. Berlin and London: Springer, 2009, pp. 31-32].

Many dyes can be used for the ultraviolet marking, but the most convenient ones for skin-surface marking are those that are commercially available to hand-stamp attendees of events. For tattooing applications, ultraviolet-absorbing injectable fluorophores are commercially available that are encapsulated within microspheres [Technical sheet for Opticz UV Blacklight Reactive Blue Invisible Ink. 2013. Blacklight.com, 26735 W Commerce Dr Ste 705, Volo, Ill. 60073-9658; Richard P. HAUGLAND. Fluorophores excited with UV light. Section 1.7 In: The Molecular Probes Handbook: A Guide to Fluorescent Probes and Labeling Technologies, 11th Edition, 2010. Molecular Probes/Life Technologies. 4849 Pitchford Ave., Eugene, Oreg. 97402. pp. 66-73; Technical sheet for BIOMATRIX System. 2013. NEWWEST Technologies, Santa Rosa Calif. 95407-0286].

Many dyes can also be used for the infrared marking, their major advantage being that auto-fluorescence from human skin or tissue generally does not interfere with detection of their fluorescence. In fact, the infrared fluorophores may be imaged up to about two centimeters under the skin. Examples of such dyes are indocyanine green and Alexa Fluor 790. Quantum dots may also be used to generate infrared fluorescence, advantages of which are that they are very stable and very brightly fluorescent. They may also be encapsulated in microspheres for purposes of tattooing. Quantum dots may also be electroluminescent, such that the electric field and currents produced by the stimulator might alone induce the emission of infrared light from the quantum dots [Richard P. HAUGLAND. Alexa Fluor Dyes Spanning the Visible and Infrared Spectrum—Section 1.3; and Qdot Nanocrystals—Section 6.6. In: The Molecular Probes Handbook: A Guide to Fluorescent Probes and Labeling Technologies, 11th Edition, 2010. Molecular Probes/Life Technologies. 4849 Pitchford Ave., Eugene, Oreg. 97402; GRAVIER J, Navarro F P, Delmas T, Mittler F, Couffin A C, Vinet F, Texier I. Lipidots: competitive organic alternative to quantum dots for in vivo fluorescence imaging. J Biomed Opt. 16 (9, 2011): 096013; ROMOSER A, Ritter D, Majitha R, Meissner K E, McShane M, Sayes C M. Mitigation of quantum dot cytotoxicity by microencapsulation. PLoS One. 6 (7, 2011):e22079:pp. 1-7; Andrew M. SMITH, Michael C. Mancini, and Shuming Nie. Second window for in vivo imaging. Nat Nanotechnol 4 (11, 2009): 710-711].

Once the patient is ready to apply the stimulator to the head (as shown in FIG. 10), he or she will place a snap-in optical attachment (50 in FIG. 5C) on the back of the smartphone, at a location on top of the rear camera (34 in FIG. 3B) and camera flash (35 in FIG. 3B), and between the electrode surfaces (33 in FIGS. 3 and 5). The purpose of the optical attachment is to facilitate optimal positioning of the electrodes, by forming a camera image of fluorescence from the spots of dye that had been placed in or under the patient's skin.

Once the snap-in optical attachment is in place, apertures are formed between the optical attachment and the rear camera/flash, as indicated by 34' and 35' in FIGS. 5A, 5B, and 5C. The optical elements shown in FIGS. 5A and 5B that are situated above the apertures are present in the smartphone, and the optical elements situated below the apertures in those figures are components of the snap-in optical attachment. The optical elements in the smartphone include a flash, which is a light-emitting diode (LED) 43 that may be programmed to provide illumination while taking a photograph (or may be even be programmed to serve as a flashlight). Without the snap-in optical attachment, light reflected back from the LED-illuminated objects would be imaged by a lens 44 that is internal to the smartphone. When the snap-in optical attachment is in place, a macro lens (56 in FIGS. 5A, 5B, and 5C) within the attachment allows for the imaging of close objects, which in this application will be fluorescence 55 emanating from the fluorescent spot of dye 59, on or under the patient's skin 58. As an example, the macro lens may be similar to ones sold by Carson Optical [LensMag™—model ML—415, Carson Optical, 35 Gilpin Avenue, Hauppauge, N.Y. 11788].

In order to produce fluorescence from the fluorescent dye in the patient's skin, the dye should be illuminated with wavelengths corresponding to peaks in its excitation spectrum. In the preferred embodiment of the invention, infrared illumination causes the dye (e.g., indocyanine green) to fluoresce at a wavelength greater than 820 nm, and the LED may be used to illuminate the dye at its excitation wavelength near 760 or 785 nm. Because the LED found in some smartphone cameras may only generate light predominantly in the visible range (400-700 nm), the optical components shown in FIG. 5A are used to shift the light towards the preferred infrared excitation wavelengths. As light leaves the LED 43 of the flash unit, it first encounters a dichroic mirror 51 that passes light with a wavelength less than 700 nm (visible light) and reflects light with wavelengths greater than 700 nm (infrared light). The light passing through the dichroic mirror then encounters a film of phosphorescent material 52 that absorbs the visible light and emits phosphorescent infrared light with a peak in the range of about 760 to 785 nm [Haifeng XIANG, Jinghui Cheng, Xiaofeng Ma, Xiangge Zhou and Jason Joseph Chruma. Near-infrared phosphorescence: materials and applications. Chem. Soc. Rev. 42(2013): 6128-6185]. If the phosphorescent infrared light is emitted back towards the LED, then the dichroic mirror 51 reflects the phosphorescence back into a chamber 53, where it joins phosphorescence that is emitted in the direction away from the LED. The chamber 53 is coated internally with a reflective material such as silver, so that the phosphorescence may undergo multiple reflections from the silver or from the dichroic mirror 51, until it eventually emerges as light from a slit 54 that is directed towards the spots on the patient's skin. Similarly, visible light that passes through the phosphorescent layer 52 without generating phosphorescence may also undergo multiple reflections from the silver coating until it encounters the phosphorescent layer 52 again, which this time may produce phosphorescence, or it may pass back through the dichroic mirror and be lost (along with first-pass visible light that is backscattered from the phosphorescent layer), unless it is reflected back through the dichroic mirror 51 from the surface of the LED. Some of the visible light that enters the chamber 53 may also emerge as light from the slit 54. However, the visible light emerging from the slit does not have wavelengths needed to produce fluorescence 55 from the infrared dye 59 in the patient's skin 58. Furthermore, any of the visible light that emerges from the slit and eventually makes its way through the macro lens 56 would be blocked by a filter 57 that passes only light having a wavelength greater than about 800 nm. Thus, the filter 57 will block not only any visible light from the LED, but also the excitation infrared wavelengths less than about 780 nm that are produced by the phosphorescent layer 52. The light that does pass through the filter 57 will be mostly fluorescence from the spot of dye 59, and that fluorescence will be imaged by the lens 44 onto the light-sensitive elements in the smartphone's rear camera, thereby producing an image of the fluorescent spot.

Note that the foregoing description presumes that there is a gap between the macro lens 56 and the patient's skin 58, such that the excitation wavelengths of light may pass under the macro lens to wherever the infrared dye 59 may be located. This would generally be the case because the height of the electrode surfaces (33' in FIGS. 5A and 5B) prevent the macro lens 56 from reaching the surface of the patient's skin. However, even if the macro lens 56 were pressed all the way to the surface of the skin, a spot of fluorescent dye 59 could still be excited by the light if it had been injected deeper than the surface of the skin. This is because infrared light may penetrate up to about 2 cm through the skin.

In the event that the LED 43 produces light with wavelengths that are suitable for excitation of the fluorescent dye, then the phosphorescent layer 52 that is shown in FIG. 5A is not necessary. For example, this would be the case if the LED 43 produces sufficient light with wavelengths around 760 nm to 785 nm, which would excite the infrared dye indocyanine green. This would also be the case if one were exciting a dye that is excited with light in the ultraviolet and violet range, producing blue fluorescence. In those cases, the snap-in optical attachment shown in FIG. 5B would be more appropriate. As shown there, a filter 51' would pass light with wavelengths only in the range that excites the fluorophore, and it therefore would not pass the wavelengths of fluorescence that are emitted by the fluorophore (or other confounding wavelengths). The excitation illumination will then enter a chamber 53' with reflective internal surfaces, such that the excitation light will appear as light emanating from a slit 54', which is directed towards the fluorophore spot 59 in or under the patient's skin 58. That excitation illumination will then cause the fluorophore spot in the patient's skin to emit fluorescent light 55, which will be collected by the macro lens 56. Light corresponding to the excitation wavelengths will also be collected by the macro lens 56, but a filter 57' will block the excitation wavelengths of light and pass only the fluorescence. The fluorescence will then be collected by the smartphone's lens 44 and be imaged onto the photosensitive material of the smartphone's camera, thereby producing an image of the fluorescent spot in or under the patient's skin.

During initial testing of the stimulator on the patient, the appropriate snap-in optical attachment will be in place (as described above), and the smartphone's camera will be turned on, while electrical impulses from the electrode surfaces 33 are applied to the patient's skin. If the electrodes are near their optimal position on the patient's skin, the fluorescent spots that had been applied to the patient's skin should then appear in an image produced by the smartphone's camera, viewable on the screen of the smartphone (31 in FIG. 3). The electrodes may then be slightly translated, rotated, and depressed into the patient's skin, until a maximum therapeutic response is achieved. Once the maximum therapeutic position of the electrodes has been decided, a reference image of the fluorescent spots will then be recorded at that position and saved in the memory of the smartphone for future reference.

Figure 6:
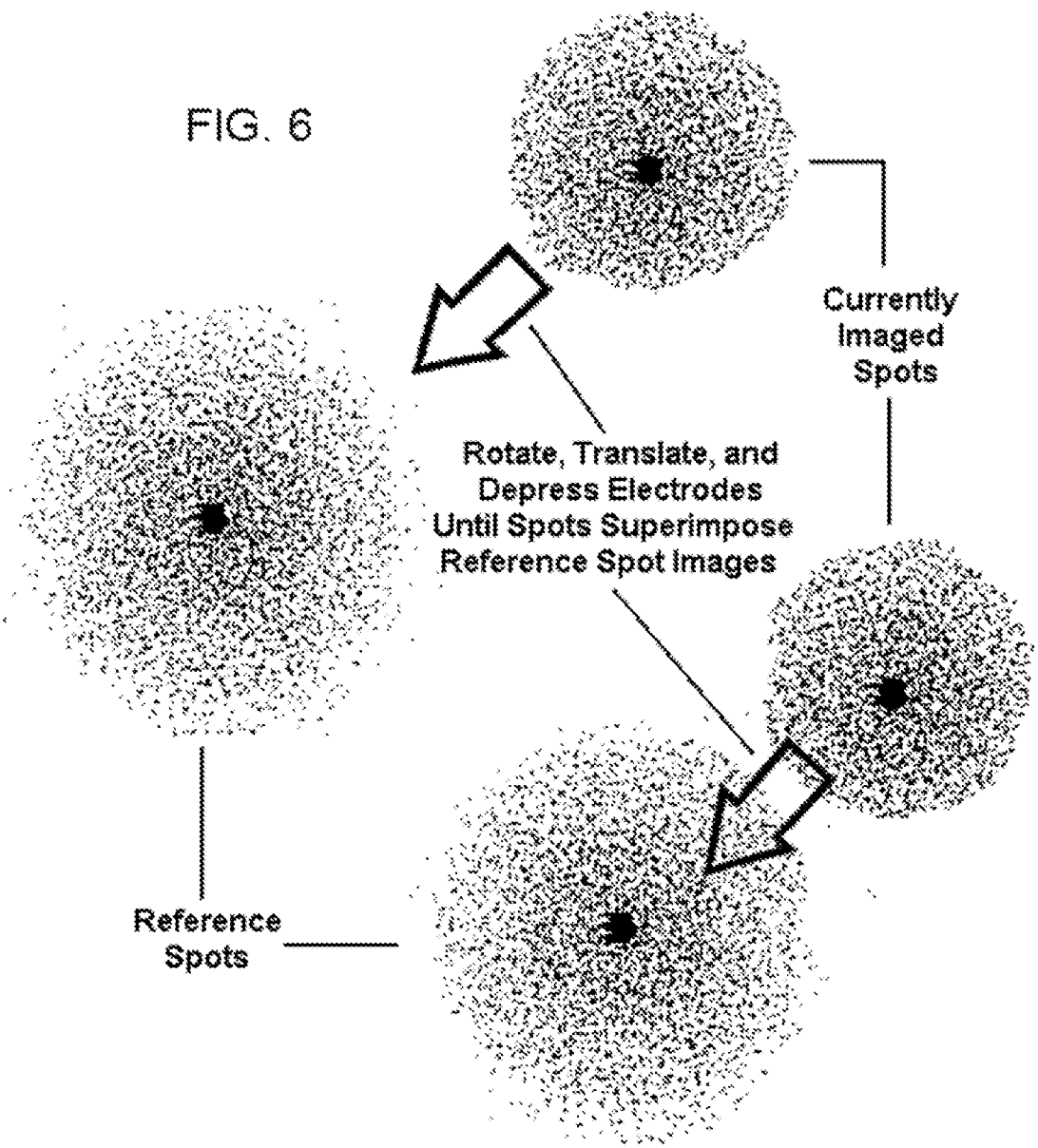
FIG. 6 shows how a continuously imaged fluorescence image of two spots is superimposed onto a reference image of those spots, in order to optimally position the stimulator.

During subsequent sessions when the patient applies the stimulator to his or her skin, the appropriate snap-in optical attachment will also be in place, and the smartphone's camera will be turned on, while electrical impulses from the electrode surfaces 33 are applied to the patient's skin. The fluorescent spots that had been applied to the patient's skin should then also appear in an image produced by the smartphone's camera, viewable on the screen of the smartphone (31 in FIG. 3). By superimposing the currently viewed image of the fluorescent spots onto the previously recorded reference image of the fluorescent spots, one may then ascertain the extent to which the current position, orientation, and depth-into-the-skin of the electrode surfaces match the previously recorded optimal reference position. This is illustrated in FIG. 6, which shows the currently imaged fluorescent spots and the superimposed reference spots, as well as the rotation and translation needed to align the former onto the latter spots. Instead of superimposing images of the current and reference images of the spots, one may also subtract the two images, pixel-by-pixel, and display the absolute value of the difference. In that case, optimal positioning of the electrode surfaces would occur when the reference image approximately nulls the current image. The sum of the pixel values in the nulled image may then be used as an index of the extent to which the current and reference images coincide. The control unit of the stimulator may also be configured to disable electrical stimulation of the selected nerve unless a pre-determined cutoff in the index of alignment of the images has been achieved. For example, use of such a fluorescent spot alignment index may be used to ensure that the patient is attempting to stimulate the nerve on the intended side of the head. It is understood, however, that the fluorescence alignment method described above may not be suitable for all patients, particularly patients having heads that are significantly wrinkled or that contain large amounts of fatty tissue.

Embodiments with a Distributed Controller

In one embodiment of the present invention, significant portions of the control of the nerve stimulation reside in controller components that are physically separate from the housing of the stimulator. In this embodiment, separate components of the controller and stimulator housing generally communicate with one another wirelessly. Thus, the use of wireless technology avoids the inconvenience and distance limitations of interconnecting cables. Additional reasons in the present disclosure for physically separating many components of the controller from the stimulator housing are as follows.

First, the stimulator may be constructed with the minimum number of components needed to generate the stimulation pulses, with the remaining components placed in parts of the controller that reside outside the stimulator housing, resulting in a lighter and smaller stimulator housing. In fact, the stimulator housing may be made so small that it could be difficult to place, on the stimulator housing's exterior, switches and knobs that are large enough to be operated easily. Instead, for the present disclosure, the user may generally operate the device using the smartphone touchscreen.

Second, the controller (330 in FIG. 1) may be given additional functions when free from the limitation of being situated within or near the stimulator housing. For example, one may add to the controller a data logging component that records when and how stimulation has been applied to the patient, for purposes of medical recordkeeping and billing. The complete electronic medical record database for the patient may be located far from the stimulator (e.g., somewhere on the internet), and the billing system for the stimulation services that are provided may also be elsewhere, so it would be useful to integrate the controller into that recordkeeping and billing system, using a communication system that includes access to the internet or telephone networks.

Third, communication from the databases to the controller would also be useful for purposes of metering electrical stimulation of the patient, when the stimulation is self-administered. For example, if the prescription for the patient only permits only a specified amount of stimulation energy to be delivered during a single session of nerve stimulation, followed by a wait-time before allowing the next stimulation, the controller can query the database and then permit the stimulation only when the prescribed wait-time has passed. Similarly, the controller can query the billing system to assure that the patient's account is in order, and withhold the stimulation if there is a problem with the account.

Fourth, as a corollary of the previous considerations, the controller may be constructed to include a computer program separate from the stimulating device, in which the databases are accessed via cell phone or internet connections.

Fifth, in some applications, it is desired that the stimulator housing and parts of the controller be physically separate. For example, when the patient is a child, one wants to make it impossible for the child to control or adjust the nerve stimulation. The best arrangement in that case is for the stimulator housing to have no touchscreen elements, control switches or adjustment knobs that could be activated by the child. Alternatively, any touchscreen elements, switches and knobs on the stimulator can be disabled, and control of the stimulation then resides only in a remote controller with a child-proof operation, which would be maintained under the control of a parent or healthcare provider.

Sixth, in some applications, the particular control signal that is transmitted to the stimulator by the controller will depend on physiological and environmental signals that are themselves transmitted to and analyzed by the controller. In such applications, many of the physiological and environmental signals may already be transmitted wirelessly, in which case it is most convenient to design an external part of the controller as the hub of all such wireless activity, including any wireless signals that are sent to and from the stimulator housing.

With these considerations in mind, an embodiment of the invention includes a base station that may send/receive data to/from the stimulator, and may send/receive data to/from databases and other components of the system, including those that are accessible via the internet. Typically, the base station will be a laptop computer attached to additional components needed for it to accomplish its function. Thus, prior to any particular stimulation session, the base station may load into the stimulator (FIG. 3) parameters of the session, including waveform parameters, or the actual waveform. See FIG. 2. In one embodiment, the base station is also used to limit the amount of stimulation energy that may be consumed by the patient during the session, by charging the stimulator's rechargable battery (see 41 in FIG. 3) with only a specified amount of releasable electrical energy, which is different than setting a parameter to restrict the duration of a stimulation session. Thus, the base station may comprise a power supply that may be connected to the stimulator's rechargable battery, and the base station meters the recharge. As a practical matter, the stimulator may therefore use two batteries, one for applying stimulation energy to the electrodes (the charge of which may be limited by the base station) and the other for performing other functions. Methods for evaluating a battery's charge or releasable energy are known in the art, for example, in U.S. Pat. No. 7,751,891, entitled Power supply monitoring for an implantable device, to ARMSTRONG et al. Alternatively, control components within the stimulator housing may monitor the amount of electrode stimulation energy that has been consumed during a stimulation session and stop the stimulation session when a limit has been reached, irrespective of the time when the limit has been reached.

Figure 7:
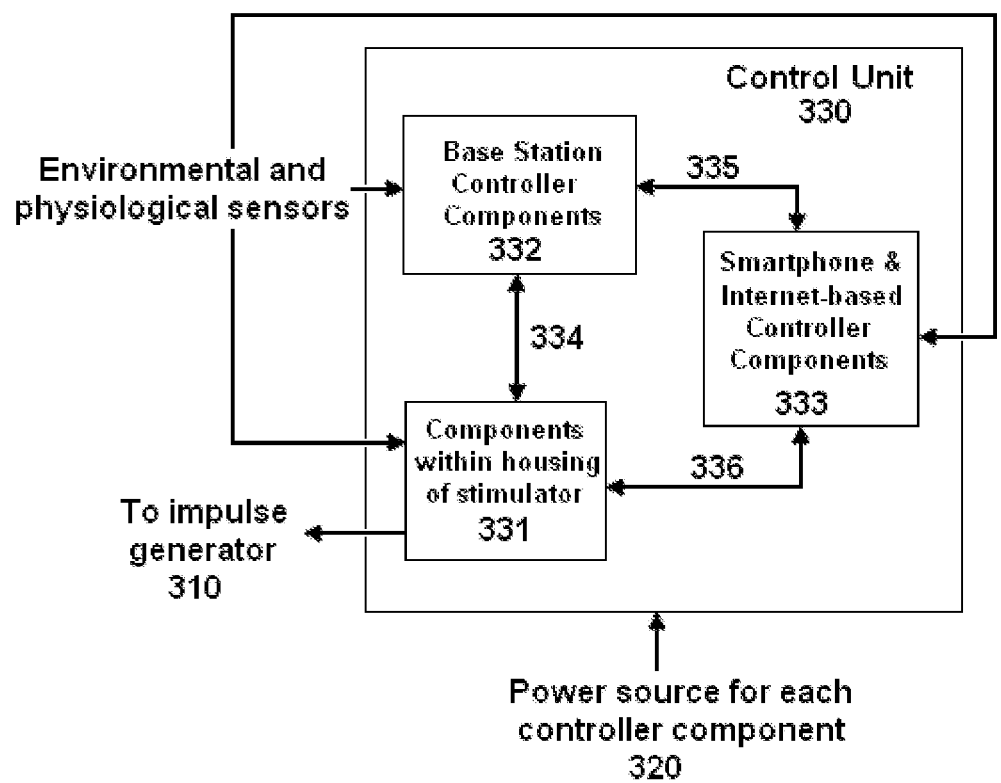
FIG. 7 shows an expanded diagram of the control unit shown in FIG. 1, separating components of the control unit into those within the housing of the stimulator, those within a base station, and those within smartphone and internet-based devices, also showing communication paths between such components.

The communication connections between different components of the stimulator's controller are shown in FIG. 7, which is an expanded representation of the control unit 330 in FIG. 1. Connection between the base station controller components 332 and components within the stimulator housing 331 is denoted in FIG. 7 as 334. Connection between the base station controller components 332 and internet-based or smartphone components 333 is denoted as 335. Connection between the components within the stimulator housing 331 and internet-based or smartphone components 333 is denoted as 336. For example, control connections between the smartphone and stimulator housing via the audio jack socket would fall under this category, as would any wireless communication directly between the stimulator housing itself and a device situated on the internet. In principle, the connections 334, 335 and 336 in FIG. 7 may be either wired or wireless. Different embodiments of the invention may lack one or more of the connections.

Although infrared or ultrasound wireless control might be used to communicate between components of the controller, they are not preferred because of line-of-sight limitations. Instead, in the present disclosure, the communication between devices preferably makes use of radio communication within unlicensed ISM frequency bands (260-470 MHz, 902-928 MHz, 2400-2.4835 GHz). Components of the radio frequency system in devices in 331, 332, and 333 typically comprise a system-on-chip transciever with an integrated microcontroller; a crystal; associated balun & matching circuitry, and an antenna [Dag GRINI. RF Basics, RF for Non-RF Engineers. Texas Instruments, Post Office Box 655303, Dallas, Tex. 75265, 2006].

Transceivers based on 2.4 GHz offer high data rates (greater than 1 Mbps) and a smaller antenna than those operating at lower frequencies, which makes them suitable for with short-range devices. Furthermore, a 2.4 GHz wireless standard (Bluetooth, Wi-Fi, and ZigBee) may be used as the protocol for transmission between devices. Although the ZigBee wireless standard operates at 2.4 GHz in most jurisdictions worldwide, it also operates in the ISM frequencies 868 MHz in Europe, and 915 MHz in the USA and Australia. Data transmission rates vary from 20 to 250 kilobits/second with that standard. Because many commercially available health-related sensors may operate using ZigBee, its use may be recommended for applications in which the controller uses feedback and feedforward methods to adjust the patient's nerve stimulation based on the sensors' values, as described below in connection with FIG. 11 [ZigBee Wireless Sensor Applications for Health, Wellness and Fitness. ZigBee Alliance 2400 Camino Ramon Suite 375 San Ramon, Calif. 94583].

A 2.4 GHz radio has higher power consumption than radios operating at lower frequencies, due to reduced circuit efficiencies. Furthermore, the 2.4 GHz spectrum is crowded and subject to significant interference from microwave ovens, cordless phones, 802.11b/g wireless local area networks, Bluetooth devices, etc. Sub-GHz radios enable lower power consumption and can operate for years on a single battery. These factors, combined with lower system cost, make sub-GHz transceivers ideal for low data rate applications that need maximum range and multi-year operating life.

The antenna length needed for operating at different frequencies is 17.3 cm at 433 MHz, 8.2 cm at 915 MHz, and 3 cm at 2.4 GHz. Therefore, unless the antenna is included in a collar or band that supports the device shown in FIG. 3, the antenna length may be a disadvantage for 433 MHz transmission. The 2.4 GHz band has the advantage of enabling one device to serve in all major markets worldwide since the 2.4 GHz band is a global spectrum standard. However, 433 MHz is a viable alternative to 2.4 GHz for most of the world, and designs based on 868 and 915 MHz radios can serve the US and European markets with a single product.

Range is determined by the sensitivity of the transceiver and its output power. A primary factor affecting radio sensitivity is the data rate. Higher data rates reduce sensitivity, leading to a need for higher output power to achieve sufficient range. For many applications that entail a low data rate, the preferred rate is 40 Kbps where the transceiver can still use a standard off-the-shelf 20 parts per million crystal.

A typical signal waveform that might be transmitted wirelessly to the stimulator housing was shown in FIGS. 2B and 2C. As seen there, individual sinusoidal pulses have a period of tau, and a burst consists of N such pulses. This is followed by a period with no signal (the inter-burst period). The pattern of a burst followed by silent inter-burst period repeats itself with a period of T. For example, the sinusoidal period tau may be 200 microseconds; the number of pulses per burst may be N=5; and the whole pattern of burst followed by silent inter-burst period may have a period of T=40000 microseconds, which is comparable to 25 Hz stimulation (a much smaller value of T is shown in FIG. 2C to make the bursts discernable). When these exemplary values are used for T and tau, the waveform contains significant Fourier components at higher frequencies (1/200 microseconds=5000/sec). Such a signal may be easily transmitted using 40 Kbps radio transmission. Compression of the signal is also possible, by transmitting only the signal parameters tau, N, T, Emax, etc., but in that case the stimulator housing's control electronics would then have to construct the waveform from the transmitted parameters, which would add to the complexity of components of the stimulator housing.

However, because it is contemplated that sensors attached to the stimulator housing may also be transmitting information, the data transfer requirements may be substantially greater than what is desired only to transmit the signal shown in FIG. 2. Therefore, the present invention may make use of any frequency band, not limited to the ISM frequency bands, as well as techniques known in the art to suppress or avoid noise and interferences in radio transmission, such as frequency hopping and direct sequence spread spectrum.

Application of the Stimulator to the Head of the Patient

In the present invention, selected nerve fibers are stimulated using the disclosed electrical stimulation devices. One objective is to stimulate the trigeminal nerve in order to treat headaches and other disorders, so the invention contemplates noninvasive stimulation of any of the branches of the trigeminal nerve that are accessible on the surface of the patient's head. In a preferred embodiment, the supraorbital and supratrochlear nerves are stimulated at a location above the orbit of the patient's eye(s) or on the patient's forehead, but other nerves of the face and head could also be stimulated according to the invention. Therefore, before describing stimulation of the preferred nerves, we describe many of the other nerves that could be stimulated instead. In addition to branches of the trigeminal nerve, they include nerves of the head that arise from the spinal cord.

Figure 8A:
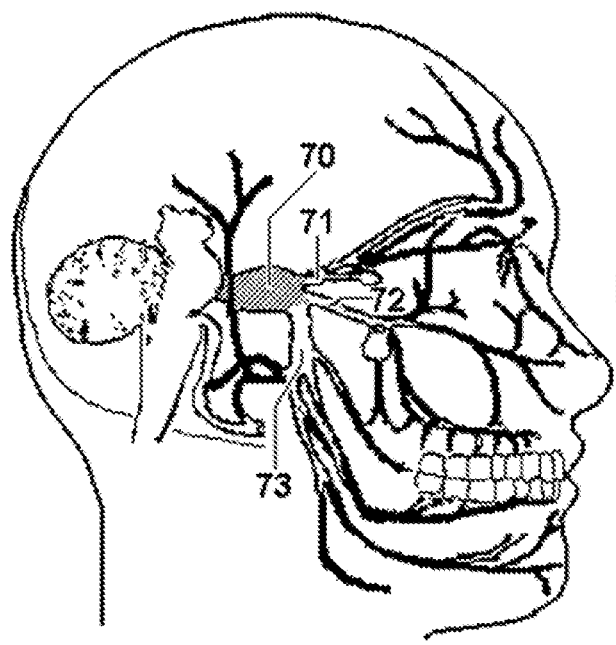
FIG. 8A illustrates branches of the trigeminal nerve that enervate much of the face and scalp.
Figure 8B:
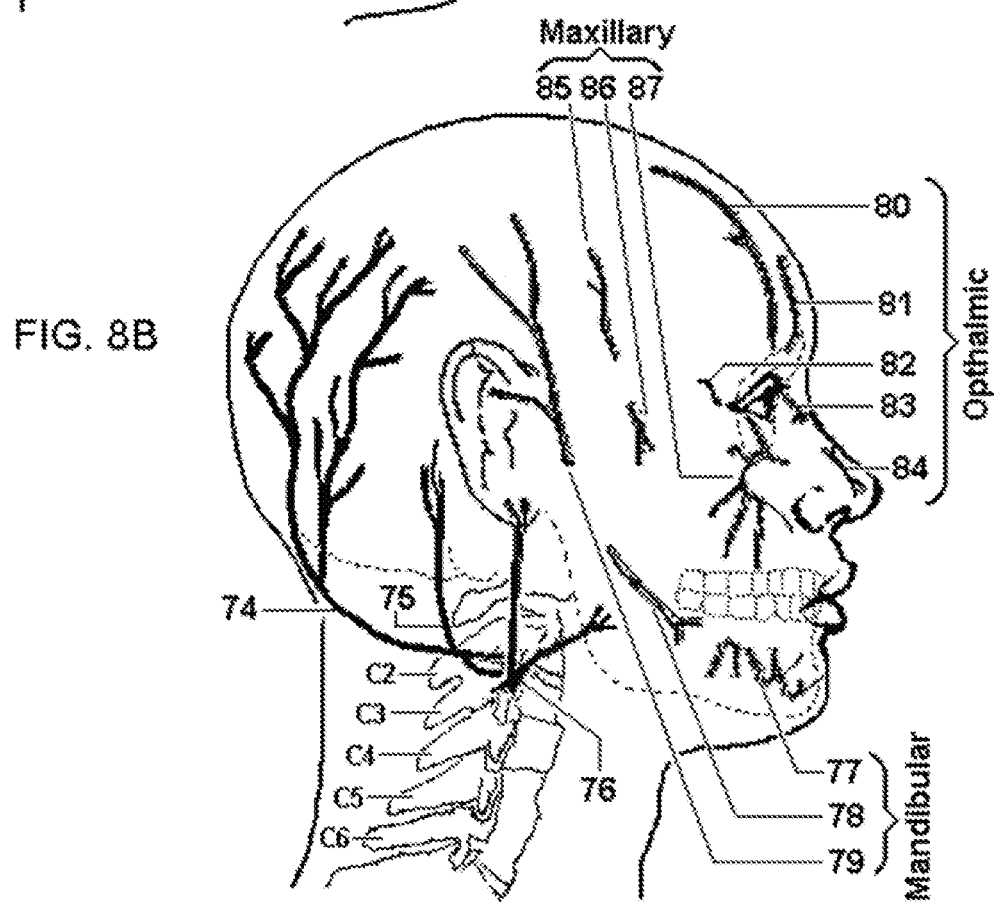
FIG. 8B illustrates the location of the main nerves that reach the surface of the head, including nerves that originate in the spine.

The nerves of the head that may be stimulated according to the present invention include those shown in FIG. 8. Many of the nerves are branches of the paired trigeminal nerves (cranial nerve V). FIG. 8A shows the internal anatomy of the trigeminal nerve and its branches, and FIG. 8B shows the location of trigeminal nerve branches that are accessible for noninvasive electrical stimulation through the skin surface of the head.

The trigeminal nerves themselves are labeled in FIG. 8A as 70 and are located on each side of the pons, owing to the fact that all trigeminal sensory fibers enter the brainstem at the level of the pons, and the trigeminal motor fibers leave the brain stem at the level of the pons [P WOOLFALL and A Coulthard. Trigeminal nerve: anatomy and pathology. The British Journal of Radiology 74(2001): 458-467]. The trigeminal nerve (70) then forms three branches, as shown in FIG. 8A: the opthalmic nerve (71), the maxillary nerve (72), and the mandibular nerve (73). The ophthalmic and maxillary nerves are purely sensory, and the mandibular nerve has both cutaneous and motor functions.

As shown in FIG. 8B, branches of the ophthalmic nerve that extend to the surface of the head include the supraorbital nerve (80), the supratrochlear nerve (81), the lacrimal nerve (82), the infratrochlear nerve (83), and the external nasal nerve (84). As also shown in FIG. 8B, branches of the maxillary nerve that extend to the surface of the head include the zygomaticotemporal nerve (85), the zygomatofacial nerve (86), and the infraorbital nerve (87).

Branches of the mandibular nerve that extend to the surface of the head include the mental nerve (77), the buccal nerve (78), and the auriculotemporal nerve (79) [SIMOPOULOS T, Bajwa Z, Lantz G, Lee S, Burstein R. Implanted auriculotemporal nerve stimulator for the treatment of refractory chronic migraine. Headache 50 (6, 2010): 1064-1069].

In addition to the above-mentioned branches of the trigeminal nerve, several other nerves of the head are spinal nerves, having their origin at cervical levels C2 and C3. As shown in FIG. 8B, they include the greater occipital nerve (74), the lesser occipital nerve (75), and the great auricular nerve (76). Disorder of the occipital nerves (74) and (75) cause cervicogenic headaches referred to as occipital neuralgias, which results in focal head pain that serves as a trigger for migraine headaches [JASPER J F, Hayek S M. Implanted occipital nerve stimulators. Pain Physician 11 (2, 2008): 187-200; SLAVIN K V, Colpan M E, Munawar N, Wess C, Nersesyan H. Trigeminal and occipital peripheral nerve stimulation for craniofacial pain: a single-institution experience and review of the literature. Neurosurg Focus 21 (6, 2005):E5, pp. 1-5]. Other spinal nerves around the posterior portion of the head or neck, such as the great auricular nerve (76), may also become irritated and cause pain that triggers headaches.

Figure 9:
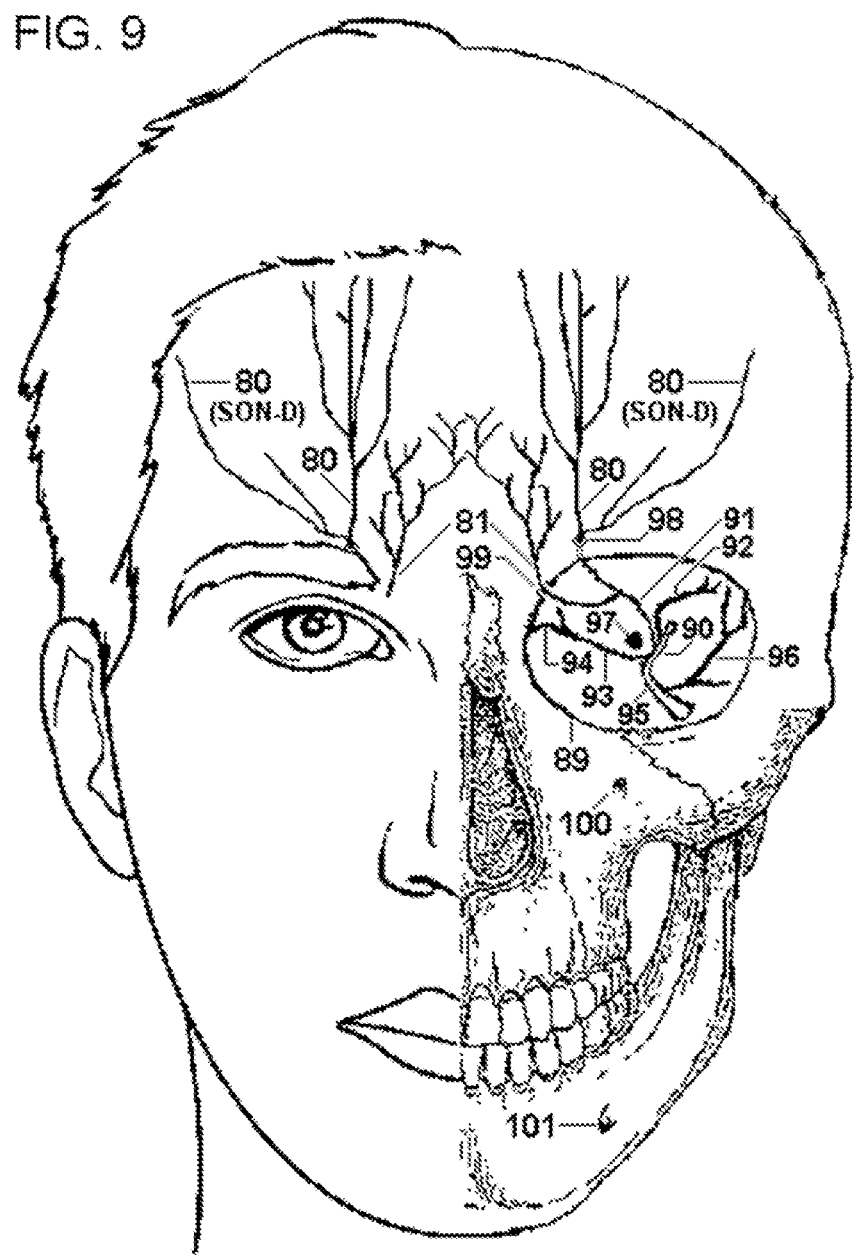
FIG. 9 illustrates nerves that leave the orbit of the eye, particularly the supraorbital nerve and the supratrochlear nerve, which exit the orbit through a foramen or a notch.

FIG. 9 shows the anatomy of two nerves of the face that are preferably stimulated according to the present invention, namely, the supraorbital nerve (80) and the supratrochlear nerve (81). These two nerves are branches of the ophthalmic branch of the trigeminal nerve (see FIG. 8). They originate within the orbit of the eye (89), behind the eyeball, and their parent branch emerges through a fissure in the orbit, the superior orbital fissure (90). As seen in FIG. 9, the parent branch of the supraorbital nerve (80) and the supratrochlear nerve (81) is the frontal nerve (91), which emerges through the superior orbital fissure (90). Other branches of the ophthalmic branch of the trigeminal nerve enter the orbit through that fissure as well—the lacrimal nerve (92) and the nasociliary nerve (93), with the latter nerve giving rise to the infratrochlear nerve (94). The oculomotor nerve (cranial nerve III), trochlear nerve (cranial nerve IV), and abducens nerve (cranial nerve VI) also enter the orbit via the superior orbital fissure (not shown). Other nerves, such as the zygomatic nerve (96) of the maxillary branch of the trigeminal nerve, enter the orbit through a different fissure, the inferior orbital fissure (95). Yet another opening, the optic foramen (97), is the opening to the optic canal, through which the optic nerve (cranial nerve II) passes.

The way in which the supraorbital nerve (80) and the supratrochlear nerve (81) leave the orbit of the eye is particularly relevant to the present invention. This is because one objective of some embodiments of the invention is to electrically stimulate those nerves at a site that is accessible outside of the orbit of the eye, but before these nerves have had a chance to form additional nerve branches within the forehead. By stimulating those nerves before they have had a chance to undergo branching, one is assured of a maximum localized stimulation effect, without the stimulation of other tissue such as the muscle in which the downstream nerve branches reside.

The supraorbital nerve (80) often exits the orbit of the eye through a foramen (hole in the skull bone) called the supraorbital foramen (98 in FIG. 9). The supratrochlear nerve (81) often exits the orbit of the eye through a notch (indentation in the skull on the edge of the orbit) called the supratrochlear notch (99). However, the supraorbital nerve (80) may exit the orbit of the eye through a notch instead of a foramen, and the first branch of the nerve may even occur within the orbit of the eye such that there are two notches or foramina. The supratrochlear nerve (81) may also exit the orbit through a foramen rather than a notch. There is also considerable variation between individuals concerning not only whether foramen or notches are present as the location of nerve exits, but also as to the actual location of the exit points under the eyebrow relative to the midline of the individual's face [ANDERSON NB, Bovim G, Sjaastad O. The frontotemporal peripheral nerves. Topographic variations of the supraorbital, supratrochlear and auriculotemporal nerves and their possible clinical significance. Surg Radiol Anat 23 (2, 2001): 97-104; MILLER T A, Rudkin G, Honig M, Elahi M, Adams J. Lateral subcutaneous brow lift and interbrow muscle resection: clinical experience and anatomic studies. Plast Reconstr Surg 105 (3, 2000): 1120-1127; WEBSTER R C, Gaunt J M, Hamdan U S, Fuleihan N S, Giandello P R, Smith R C. Supraorbital and supratrochlear notches and foramina: anatomical variations and surgical relevance. Laryngoscope 96 (3, 1986): 311-315; SAYLAM C, Ozer M A, Ozek C, Gurler T. Anatomical variations of the frontal and supraorbital transcranial passages. J Craniofac Surg 14 (1, 2003): 10-12; MISHRA A, Shrestha S, Singh M. Varying positions and anthropometric measurement of supraorbital and supratrochlear canal/foramen in adult human skulls. Nepal Med Coll J 15 (2, 2013): 133-136; JANIS J E, Hatef D A, Hagan R, Schaub T, Liu J H, Thakar H, Bolden K M, Heller J B, Kurkjian T J. Anatomy of the supratrochlear nerve: implications for the surgical treatment of migraine headaches. Plast Reconstr Surg 131 (4, 2013): 743-750; D. J. TRIVEDI, P. S. Shrimankar, V. B. Kariya, C. A. Pensi. A Study Of Supraorbital Notches And Foramina In Gujarati Human Skulls. NJIRM 2010; 1 (3, 2010): 1-6; FALLUCO M, Janis J E, Hagan R R. The anatomical morphology of the supraorbital notch: clinical relevance to the surgical treatment of migraine headaches. Plast Reconstr Surg 130 (6, 2012): 1227-1233].

Such inter-individual anatomical variation is also observed for other nerves of the head that are shown in FIG. 8B [JEONG S M, Park K J, Kang S H, Shin H W, Kim H, Lee H K, Chung Y G. Anatomical consideration of the anterior and lateral cutaneous nerves in the scalp. J Korean Med Sci 25 (4, 2010): 517-522].

Because it is important in the present invention to accurately locate the foramen and notch for each individual, in a preferred embodiment the locations are determined by computed tomography or ultrasound, rather than by feeling about the orbit of the eye [TURHAN-Haktanir N, Ayçiçek A, Haktanir A, Demir Y. Variations of supraorbital foramina in living subjects evaluated with multidetector computed tomography. Head Neck 30 (9, 2008): 1211-1215; SPINNER D, Kirschner J S. Accuracy of ultrasound-guided superficial trigeminal nerve blocks using methylene blue in cadavers. Pain Med 13 (11, 2012): 1469-1473]

Once the supraorbital nerve (80) has left the orbit of the eye, it branches into regions of the forehead through muscle. This involves not only superficial branching, but also deeper branching of the supraorbital nerve (SON-D) in FIG. 9. Individuals may differ anatomically with regard to the branching patterns [JANIS J E, Ghavami A, Lemmon J A, Leedy J E, Guyuron B. The anatomy of the corrugator supercilii muscle: part II. Supraorbital nerve branching patterns. Plast Reconstr Surg 121 (1, 2008): 233-240].

Implanted electrodes have been used to stimulate the supraorbital and supratrochlear nerves. The stimulation leads are similar to those used in other neurostimulation applications such as spinal cord stimulation, and the leads are placed across the supraorbital ridge, but not in very close proximity to the supraorbital and supratrochlear foramen and notches alone [AMIN S, Buvanendran A, Park K S, Kroin J S, Moric M. Peripheral nerve stimulator for the treatment of supraorbital neuralgia: a retrospective case series. Cephalalgia 28 (4, 2008): 355-359; ASENSIO-Samper JM1, Villanueva V L, Pérez A V, López M D, Monsalve V, Moliner S, De Andrés J. Peripheral neurostimulation in supraorbital neuralgia refractory to conventional therapy. Pain Pract 8 (2, 2008): 120-124; NAROUZE S N, Kapural L. Supraorbital nerve electric stimulation for the treatment of intractable chronic cluster headache: a case report. Headache 47(2007):1100-1102; SLAVIN K V, Colpan M E, Munawar N, Wess C, Nersesyan H. Trigeminal and occipital peripheral nerve stimulation for craniofacial pain: a single-institution experience and review of the literature. Neurosurg Focus 21 (6, 2005):E5, pp. 1-5; VAISMAN J, Markley H, Ordia J, Deer T. The treatment of medically intractable trigeminal autonomic cephalalgia with supraorbital/supratrochlear stimulation: a retrospective case series. Neuromodulation 15 (4, 2012): 374-380].

Surface electrodes have also been used to stimulate the supraorbital and supratrochlear nerves. However, here too the leads are placed across the temple, but not in very close proximity to the supraorbital and supratrochlear foramen and notches alone [U.S. Pat. No. 8,428,734, entitled Device for the electrotherapeutic treatment of tension headaches, to RIGAUX et al.; GERARDY P Y, Fabry D, Fumal A, Schoenen J: A pilot study on supra-orbital surface electrotherapy in migraine. Cephalalgia 29(2009):134 (poster session); PIQUET M, Balestra C, Sava S L. Supraorbital transcutaneous neurostimulation has sedative effects in healthy subjects. BMC Neurol 11(2011): 135, pp. 1-7; MAGIS D, Sava S, D Elia T S, Baschi R, Schoenen J. Safety and patients' satisfaction of transcutaneous Supraorbital NeuroStimulation (tSNS) with the Cefaly® device in headache treatment: a survey of 2,313 headache sufferers in the general population. J Headache Pain. 14 (1, 2013): 95, pp. 1-8; SCHOENEN J, Vandersmissen B, Jeangette S, Herroelen L, Vandenheede M, Gerard P, Magis D. Migraine prevention with a supraorbital transcutaneous stimulator: a randomized controlled trial. Neurology 80 (8, 2013): 697-704; Food and Drug Administration. Submission No. K122566. Device Name Cefaly. Transcutaneous Electrical Nerve Stimulator to Treat Headache. Dec. 13, 2012. FDA. 10903 New Hampshire Ave Silver Spring, Md. 20993-0002]

FIG. 10 illustrates use of the nerve stimulator according to embodiments of the present invention, when positioned to stimulate supraorbital and supratrochlear nerves, when applied to different locations on the head of the patient. As described above, the stimulator comprises a smartphone (31) with its back cover removed and and joined to a housing (32) that comprises a pair of electrode surfaces (33) along with circuitry to control and power the electrodes and interconnect with the smartphone. For simplicity of labeling, the device 30 in the FIG. 10 corresponds to items 31 plus 32 in FIG. 3. FIG. 10A and FIG. 10B show unilateral and bilateral stimulation, respectively, of the nerves when one or two electrodes, respectively, of the stimulator are applied in the vicinity of supraorbital and supratrochlear foramen or notches. FIG. 10C shows bilateral stimulation with the electrodes positioned higher on the forehead.

In FIG. 10A, the electrode surface 33 in the vicinity of the supraorbital and supratrochlear foramen and notches is preferably masked as in FIG. 4A (item 353) so that there is a relatively high current density in the vicinity of the nerves as they exit the foramen and notch. The other electrode surface is positioned higher on the temple to produce unilateral stimulation, so that no such masking is needed for that other electrode, unless stimulation of particular downstream branches are to be selectively stimulated. If the distance between the patient's supraorbital and infraorbital foramina is comparable to the distance between the electrodes of the stimulator, one may instead position the other electrode surface over the infraorbital foramen (with masking as in FIG. 4A, item 353) so as to simultaneously stimulate nerves from two main branches of the trigeminal nerve, the opthalmic and maxillary.

In FIG. 10B, both left and right supraorbital and supratrochlear nerves are stimulated in the vicinity of their corresponding foramina and notches. Therefore, the pair of electrode surfaces 33 would preferably masked as in FIG. 4A (item 353) so that there is a relatively high current density in the vicinity of the nerves as they exit the respective foramen and notch. In FIG. 10C, the position of the smartphone electrodes is similar to what has been described in previous noninvasive stimulation of the supraorbital and supratrochlear nerves [U.S. Pat. No. 8,428,734, entitled Device for the electrotherapeutic treatment of tension headaches, to RIGAUX et al.]. In that case, no masking is needed for the electrodes unless particular downstream branches are to be selectively stimulated.

Although the previous discussion has been concerned with stimulating the supraorbital and supratrochlear nerves preferably in the vicinity of their corresponding foramen and notch, the discussion applies equally well to stimulation in the vicinity of a foramen for other branches of the trigeminal nerve. Thus, the infraorbital nerve (87 in FIG. 8) is a branch of the maxillary nerve that exits through the infraorbital foramen (100 in FIG. 9). Similarly, the mental nerve (77 in FIG. 8) is a branch of the maxillary nerve that exits through the mental foramen (101 in FIG. 9). To stimulate those nerves, according to the invention, one would mask off an area of the stimulator (353 in FIG. 4) to correspond to the immediate vicinity of the foramen [SPINNER D, Kirschner J S. Accuracy of ultrasound-guided superficial trigeminal nerve blocks using methylene blue in cadavers. Pain Med 13 (11, 2012): 1469-1473]. Stimulation of the infraorbital or mental nerves would be particularly useful for the treatment of trigeminal neuralgia. This is because the opthalmic branch of the trigeminal nerve (V1) is only infrequently associated with the neuralgia [Luke BENNETTO, Nikunj K Patel, Geraint Fuller. Trigeminal neuralgia and its management. BMJ 334 (7586, 2007): 201-205]. Stimulation of those nerves would also be useful for the treatment of other facial pain that is not associated with the ophthalmic nerve, such as dental pain.

Figure 10E:
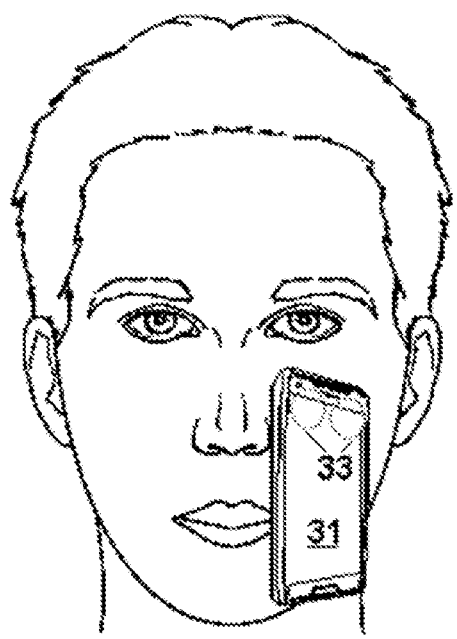
Figure 10F:
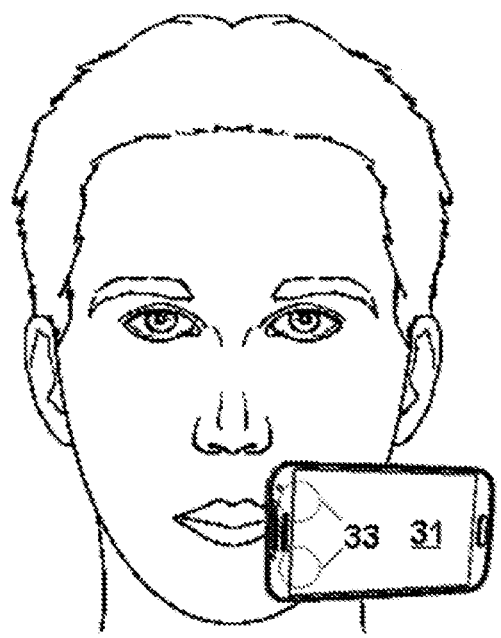
FIG. 10F, FIG. 10G, and FIG. 10H show stimulation of the mental nerve when one of the electrodes is applied in the vicinity of the mental foramen.
Figure 10G:
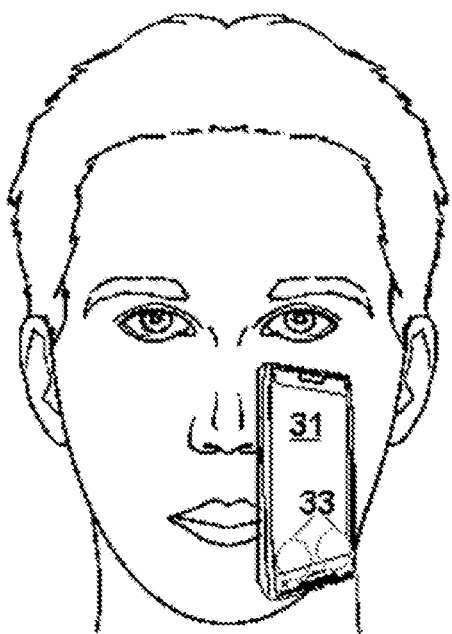
Figure 10H:
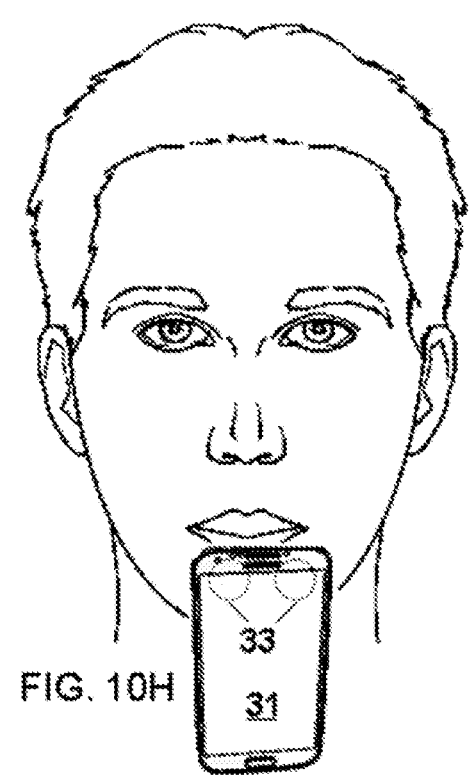

Thus, an advantage of the present invention is that it may be used to treat nerves corresponding to all three branches of the trigeminal nerve, in each case by confining much of the stimulation to small areas near the sites where a nerve emerge near the skin surface from deeper neural tissue (i.e., with high stimulation current density in the vicinity of the foramina). FIG. 10D and FIG. 10E show stimulation of the infraorbital nerve when one of the electrodes is applied in the vicinity of the infraorbital foramen. In FIG. 10D, the upper electrode is situated on the infraorbital foramen, and in FIG. 10E, the left electrode is situated there. FIG. 10F, FIG. 10G, and FIG. 10H show stimulation of the mental nerve when one of the electrodes is applied in the vicinity of the mental foramen. In FIG. 10F, the lower electrode is situated on the mental foramen; in FIG. 10G, the left electrode is situated there; and in FIG. 10H, the right electrode is situated there, with the left electrode possibly also reaching the left mental foramen, depending on the patient's anatomy. Of course, the smartphone may be rotated about the corresponding foramen to find the optimum therapeutic position. It may also be placed at a position on the head that does not correspond to a nerve exiting a foramen or notch, in order to stimulate other nerves shown in FIG. 8B.

Methods of treating a patient comprise stimulating the nerve of the head as indicated in FIGS. 8, 9, and 10, using the electrical stimulation devices that are disclosed here. Stimulation may be performed on the left or right sides of the head (i.e., unilaterally or bilaterally) or on both sides simultaneously or alternately. The position and angular orientation of the device are adjusted about that location until the patient perceives stimulation when current is passed through the stimulator electrodes. The applied current is increased gradually, first to a level wherein the patient feels sensation from the stimulation. The power is then increased, but is set to a level that is less than one at which the patient first indicates any discomfort. Straps, headbands, harnesses, or frames may be used to maintain the stimulator in position. The stimulator signal may have a frequency and other parameters that are selected to produce a therapeutic result in the patient, i.e., stimulation parameters for each patient are adjusted on an individualized basis. Ordinarily, the amplitude of the stimulation signal is set to the maximum that is comfortable for the patient, and then the other stimulation parameters are adjusted.

The stimulation is then performed with a sinusoidal burst waveform like that shown in FIG. 2. As seen there, individual sinusoidal pulses have a period of and a burst consists of N such pulses. This is followed by a period with no signal (the inter-burst period). The pattern of a burst followed by silent inter-burst period repeats itself with a period of T. For example, the sinusoidal period τ may be between about 50-1000 microseconds (equivalent to about 1-20 KHz), preferably between about 100-400 microseconds (equivalent to about 2.5-10 KHz), more preferably about 133-400 microseconds (equivalent to about 2.5-7.5 KHZ) and even more preferably about 200 microseconds (equivalent to about 5 KHz); the number of pulses per burst may be N=1-20, preferably about 2-10 and more preferably about 5; and the whole pattern of burst followed by silent inter-burst period may have a period T comparable to about 10-100 Hz, preferably about 15-50 Hz, more preferably about 25-35 Hz and even more preferably about 25 Hz (a much smaller value of T is shown in FIG. 2C to make the bursts discernable). When these exemplary values are used for T and the waveform contains significant Fourier components at higher frequencies ($\frac{1}{200}$ microseconds=5000/sec), as compared with those contained in transcutaneous nerve stimulation waveforms, as currently practiced.

When a patient is using the stimulation device to perform self-stimulation therapy, e.g., at home or at a workplace, he or she will follow the steps that are now described. It is assumed that the optimal stimulation position has already been marked on the patient's head, as described above and that a reference image of the fluorescent spots has already been acquired. The previous stimulation session will ordinarily have discharged the rechargeable batteries of the stimulator housing, and between sessions, the base station will have been used to recharged the stimulator at most only up to a minimum level. If the stimulator's batteries had charge remaining from the previous stimulation session, the base station will discharge the stimulator to a minimum level that will not support stimulation of the patient.

The patient can initiate the stimulation session using the mobile phone or base station (e.g., laptop computer) by invoking a computer program (on the laptop computer or through an app on the mobile phone) that is designed to initiate use of the stimulator. The programs in the smartphone and base station may initiate and interact with one another wirelessly, so in what follows, reference to the program (app) in the smartphone may also apply to the program in the base station, because both may be operating in tandem. For security reasons, the program would begin with the request for a user name and a password, and that user's demographic information and any data from previous stimulator experiences would already be associated with it in the login account. The smartphone may also be used to authenticate the patient using a fingerprint or voice recognition app, or other reliable authentication methods. If the patient's physician has not authorized further treatments, the base station will not charge the stimulator's batteries, and instead, the computer program will call or otherwise communicate with the physician's computer requesting authorization. After authorization by the physician is received, the computer program (on the laptop computer or through an app on the mobile phone) may also query a database that is ordinarily located somewhere on the internet to verify that the patient's account is in order. If it is not in order, the program may then request prepayment for one or more stimulation sessions, which would be paid by the patient using a credit card, debit card, PayPal or the like. The computer program will also query its internal database or that of the base station to determine that sufficient time has elapsed between when the stimulator was last used and the present time, to verify that any required wait-time has elapsed.

Having received authorization to perform a nerve stimulation session, the patient interface computer program will then ask the patient questions that are relevant to the selection of parameters that the base station will use to make the stimulator ready for the stimulation session. The questions that the computer program asks are dependent on the condition for which the patient is being treated, which for present purposes is considered to be treatment for a migraine headache. That headache may in principle be in any of the headache phases (prodrome, aura, headache pain, postdrome, and interictal period), which would be ascertained through the computer program's questions. The questions may be things like (1) is this an acute or prophylactic treatment? (2) if acute, then how severe is your headache, how long have you had it, (3) has anything unusual or noteworthy occurred since the last stimulation?, etc. In general, the types of posed questions are ones that would be placed in a headache diary [TASSORELLI C, Sances G, Allena M, Ghiotto N, Bendtsen L, Olesen J, Nappi G, Jensen R. The usefulness and applicability of a basic headache diary before first consultation: results of a pilot study conducted in two centres. Cephalalgia 28 (10, 2008): 1023-1030].

Having received such preliminary information from the patient, the computer programs will perform instrument diagnostic tests and make the stimulator ready for the stimulation session. In general, the algorithm for setting the stimulator parameters will have been decided by the physician and will include the extent to which the stimulator batteries should be charged, which the nerve should be stimulated (right or left side of the head, or both), and the time that the patient should wait after the stimulation session is ended until initiation of a subsequent stimulation session. The computer will query the physician's computer to ascertain whether there have been any updates to the algorithm, and if not, will use the existing algorithm. The patient will also be advised of the stimulation session parameter values by the interface computer program, so as to know what to expect.

Once the base station has been used to charge the stimulator's batteries to the requisite charge, the computer program (or smartphone app) will indicate to the patient that the stimulator is ready for use. At that point, the patient would attach to the smartphone the optical attachment 50 shown in FIG. 5, clean the electrode surfaces, and make any other preliminary adjustments to the hardware. The stimulation parameters for the session will be displayed, and any options that the patient is allowed to select may be made. Once the patient is ready to begin, he or she will press a "start" button on the touchscreen and may begin the nerve stimulation, as shown in FIG. 10.

Multiple methods may be used to test whether the patient is properly attempting to stimulate the nerve on the intended side of the head. For example, accelerometers and gyroscopes within the smartphone may be used to determine the position and orientation of the smartphone's touch screen relative to the patient's expected view of the screen, and a decision by the stimulator's computer program as to which hand is being used to hold the stimulator may be made by measuring capacitance on the outside of the stimulator body, which may distinguish fingers wrapped around the device versus the ball of a thumb [Raphael WIMMER and Sebastian Boring. HandSense: discriminating different ways of grasping and holding a tangible user interface. Proceedings of the 3rd International Conference on Tangible and Embedded Interaction, pp. 359-362. ACM New York, N.Y., 2009]. Pressing of the electrodes against the skin will result in a resistance drop across the electrodes, which can initiate operation of the rear camera. A fluorescent image should appear on the smartphone screen only if the device is applied to the side of the head in the vicinity of the fluorescent spots that had been applied as a tattoo earlier. If the totality of these data indicates to the computer program that the patient is attempting to stimulate the wrong nerve or that the device is being held improperly, the stimulation will be withheld, and the stimulator may then communicate with the patient via the interface computer program (in the mobile phone or laptop computer) to alert the patient of that fact. The program may then offer suggestions on how to better apply the device to the head.

However, if the stimulator is being properly applied, and an image of the fluorescent spots on the patient's head appears on the screen of the phone, the stimulator begins to stimulate according to predetermined initial stimulus parameters. The patient will then adjust the position and angular orientation of the stimulator about what he or she thinks is the correct head position, until he or she perceives stimulation when current is passed through the stimulator electrodes. An attempt is also made to superimpose the currently viewed fluorescence image of the head spots with the previously acquired reference image. The applied current is increased gradually using keys on the keyboard of the base station or on the smartphone touchscreen, first to a level wherein the patient feels sensation from the stimulation. The stimulation amplitude is then increased by the patient, but is set to a level that is less than one at which he first senses any discomfort. By trial and error, the stimulation is then optimized by the patient, who tries to find the greatest acceptable sensation with the lowest acceptable stimulation amplitude, with the stimulator aligned using the fluorescent spots. If the stimulator is being held in place by hand, it is likely that there may be inadvertent fluctuating movement of the stimulator, due for example to movement during respiration. Such relative movements will affect the effectiveness of the stimulation. However, they may be monitored by accelerometers and gyroscopes within the smartphone, which may be transmitted as movement data from the stimulator to the patient interface computer program (in the mobile phone or laptop computer). The relative movements may also be monitored and measured as fluctuations in the position of the fluorescence spots that are being imaged. By watching a graphical display of the relative movements shown by the patient interface computer program, the patient may use that display in an attempt to deliberately minimize the movements. Otherwise, the patient may attempt to adjust the amplitude of the stimulator as compensation for movement of the stimulator away from its optimum position. In a section that follows, it is described how the stimulator itself may modulate the amplitude of the stimulation in order to make such compensations.

During the session, the patient may lift the stimulator from his head, which will be detected as an increase in resistance between the electrodes and a loss of the fluorescent image of the spots on the patient's head. When that occurs, the device will withhold power to the stimulator for reasons of safety. The patient can then reapply the stimulator to his head to resume the session, although the interruption of stimulation will be recognized and recorded by the computer program. Stimulation by the patient will then continue until the battery of the stimulator is depleted, or the patient decides to terminate the stimulation session. At that point, the patient will acknowledge that the stimulation session is finished by touching a response button on the smartphone screen, whereupon the stimulator will transfer to the base station data that its microprocessor has caused to be stored regarding the stimulation session (e.g., stimulation amplitude as a function of time and information about movements of the device during the session, duration of the stimulation, the existence of interruptions, etc.). Such information will then be transmitted to and displayed by the patient interface computer program (in the mobile phone or laptop computer), which will subsequently ask the patient questions regarding the effectiveness of the stimulation. Such questions may be in regards to the post-stimulation severity of the headache, whether the severity decreased gradually or abruptly during the course of the stimulation, and whether anything unusual or noteworthy occurred during the stimulation. All such post-stimulation data will also be delivered over the internet by the patient interface computer program to the physician's computer for review and possible adjustment of the algorithm that is used to select stimulation parameters and regimens. It is understood that the physician will adjust the algorithm based not only on the experience of each individual patient, but on the experience of all patients collectively so as to improve effectiveness of the stimulator's use, for example, by identifying characteristics of most and least responsive patients.

Before logging off of the interface computer program, the patient may also review database records and summaries about all previous treatment sessions, so as to make his or her own judgment about treatment progress. If the stimulation was part of a prophylactic treatment regimen that was prescribed by the patient's physician, the patient interface computer program will remind the patient about the schedule for the upcoming self-treatment sessions and allow for a rescheduling if necessary.

In certain embodiments, a trigeminal nerve stimulation treatment according to the present invention is conducted for continuous period of thirty seconds to thirty minutes, preferably about 90 seconds to about 5 minutes and more preferably about two minutes (each defined as a single dose). After a dose has been completed, the therapy is stopped for a period of time (depending on the treatment as described below). For prophylactic treatments, the therapy preferably comprises multiple doses/day over a period of time that may last from one week to a number of years. In certain embodiments, the treatment will comprise multiple doses at predetermined times during the day and/or at predetermined intervals throughout the day. In exemplary embodiments, the treatment comprises one of the following: (1) 3 doses/day at predetermined intervals or times; (2) two doses, either consecutively, or separated by 5 min at predetermined intervals or times, preferably two or three times/day; (3) 3 doses, either consecutively or separated by 5 min again at predetermined intervals or times, such as 2 or 3 times/day; or (4) 1-3 doses, either consecutively or separated by 5 min, 4-6 times per day. Initiation of a treatment may begin when the patient experiences an acute symptom, such as a migraine, or in a risk factor reduction program it may be performed throughout the day beginning after the patient arises in the morning.

In an exemplary embodiment, each treatment session comprises 1-3 doses administered by the patient either consecutively or separated by 5 minutes. The treatment sessions are administered every 15, 30, 60 or 120 minutes during the day such that the patient could receive 2 doses every hour throughout a 24-hour day.

For certain disorders, the intervals between treatment sessions may be the most important as applicant has determined that stimulation of the trigeminal nerve can have a prolonged effect on the inhibitor neurotransmitters levels in the brain, e.g., at least one hour, up to 3 hours and sometimes up to 8 hours. In one embodiment, a treatment according to the present invention comprises one or more doses (i.e., treatment sessions) administered at intervals during a 24-hour period. In a preferred embodiment, there are 1-5 such treatment sessions, preferably 2-4 treatment sessions. Each treatment session preferably comprises 1-3 doses, each lasting between about 60 seconds to about three minutes, preferably about 90 seconds to about 150 seconds, more preferably about 2 minutes.

For an acute treatment, such as treatment of headache symptoms, the therapy according to the present invention may comprise one or more embodiments: (1) 1 dose at the onset of symptoms; (2) 1 dose at the onset of symptoms, followed by another dose at 5-15 min; or (3) 1 dose every 15 minutes to 1 hour at the onset of symptoms until the acute attack has been mitigated or aborted. In these embodiments, each dose preferably last between about 60 seconds to about three minutes, preferably about 90 seconds to about 150 seconds, more preferably about 2 minutes.

For long term treatment, the therapy may consist of: (1) 3 treatments/day; (2) 2 treatments, either consecutively or separated by 5 min, 3×/day; (3) 3 treatments, either consecutively or separated by 5 min, 2×/day; (4) 2 or 3 treatments, either consecutively or separated by 5 min, up to 10×/day; or (5) 1, 2 or 3 treatments, either consecutively or separated by 5 min, every 15, 30, 60 or 120 min.

In some embodiments of the invention, pairing of nerve stimulation may be with a additional sensory stimulation. The paired sensory stimulation may be bright light, sound, tactile stimulation, or electrical stimulation of the tongue to simulate odor/taste, e.g., pulsating with the same frequency as the nerve electrical stimulation. The rationale for paired sensory stimulation is the same as simultaneous, paired stimulation of nerves on both sides of the head, namely, that the pair of signals interacting with one another in the brain may result in the formation of larger and more coherent neural ensembles than the neural ensembles associated with the individual signals, thereby enhancing the therapeutic effect. This pairing may be considered especially when some such corresponding sensory circuit of the brain is thought to be partly responsible for triggering the migraine headache.

Selection of stimulation parameters to preferentially stimulate particular regions of the brain may be done empirically, wherein a set of stimulation parameters are chosen, and the responsive region of the brain is measured using fMRI or a related imaging method [CHAE J H, Nahas Z, Lomarev M, Denslow S, Lorberbaum J P, Bohning D E, George M S. A review of functional neuroimaging studies of vagus nerve stimulation (VNS). J Psychiatr Res. 37(6, 2003): 443-455; CONWAY C R, Sheline Y I, Chibnall J T, George M S, Fletcher J W, Mintun M A. Cerebral blood flow changes during vagus nerve stimulation for depression. Psychiatry Res. 146(2, 2006): 179-84]. Thus, by performing the imaging with different sets of stimulation parameters, a database may be constructed, such that the inverse problem of selecting parameters to match a particular brain region may be solved by consulting the database.

The individualized selection of parameters for the nerve stimulation protocol may based on trial and error in order to obtain a beneficial response without the sensation of skin pain or muscle twitches. Alternatively, the selection of parameter values may involve tuning as understood in control theory, as described below. It is understood that parameters may also be varied randomly in order to simulate normal physiological variability, thereby possibly inducing a beneficial response in the patient [Buchman T G. Nonlinear dynamics, complex systems, and the pathobiology of critical illness. Curr Opin Crit Care 10 (5, 2004): 378-82].

Use of Control Theory Methods to Improve Treatment of Individual Patients

The nerve stimulation may employ methods of control theory (e.g., feedback) in an attempt to compensate for motion of the stimulator relative to the selected nerve and to avoid potentially dangerous situations such as excessive heart rate. Thus, with these methods, the parameters of the nerve stimulation may be changed automatically, depending on environmental signals or on physiological measurements that are made, in attempt to maintain the values of the physiological signals within predetermined ranges.

When stimulating the selected nerve, motion variability may often be attributable to the patient's breathing, which involves contraction and associated change in geometry of the sternocleidomastoid muscle. Modulation of the stimulator amplitude to compensate for this variability may be accomplished by measuring the patient's respiratory phase, or more directly by measuring movement of the stimulator, then using controllers (e.g., PID controllers) that are known in the art of control theory, as now described.

FIG. 11 is a control theory representation of the disclosed nerve stimulation methods. The "System" (patient) receives input from the "Environment." For example, the environment would include ambient temperature, light, and sound, all of which may be triggers of a migraine attack. If the "System" is defined to be only a particular physiological component of the patient, the "Environment" may also be considered to include physiological systems of the patient that are not included in the "System". Thus, if some physiological component can influence the behavior of another physiological component of the patient, but not vice versa, the former component could be part of the environment and the latter could be part of the system. On the other hand, if it is intended to control the former component to influence the latter component, then both components should be considered part of the "System."

The system also receives input from the "Controller", which in this case may comprise the nerve stimulation device, as well as electronic components that may be used to select or set parameters for the stimulation protocol (amplitude, frequency, pulse width, burst number, etc.) or alert the patient as to the need to use or adjust the stimulator (i.e., an alarm). For example, the controller may comprise the control unit 330 in FIG. 1. Feedback in the schema shown in FIG. 11 is possible because physiological measurements of the System are made using sensors. Thus, the values of variables of the system that could be measured define the system's state ("the System Output"). As a practical matter, only some of those measurements are actually made, and they represent the "Sensed Physiological Input" to the Controller.

The preferred sensors will include ones ordinarily used for ambulatory monitoring. For example, the sensors may comprise those used in conventional Holter and bedside monitoring applications, for monitoring heart rate and variability, ECG, respiration depth and rate, core temperature, hydration, blood pressure, brain function, oxygenation, skin impedance, and skin temperature. The sensors may be embedded in garments or placed in sports wristwatches, as currently used in programs that monitor the physiological status of soldiers [G. A. SHAW, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington Mass. 1 Nov. 2004, pp. 1-141]. The ECG sensors should be adapted to the automatic extraction and analysis of particular features of the ECG, for example, indices of P-wave morphology, as well as heart rate variability indices of parasympathetic and sympathetic tone. Measurement of respiration using noninvasive inductive plethysmography, mercury in silastic strain gauges or impedance pneumography is particularly advised, in order to account for the effects of respiration on the heart. A noninvasive accelerometer may also be included among the ambulatory sensors, in order to identify motion artifacts. An event marker may also be included in order for the patient to mark relevant circumstances and sensations.

For brain monitoring, the sensors may comprise ambulatory EEG sensors [CASSON A, Yates D, Smith S, Duncan J, Rodriguez-Villegas E. Wearable electroencephalography. What is it, why is it needed, and what does it entail? IEEE Eng Med Biol Mag. 29 (3, 2010): 44-56] or optical topography systems for mapping prefrontal cortex activation [Atsumori H, Kiguchi M, Obata A, Sato H, Katura T, Funane T, Maki A. Development of wearable optical topography system for mapping the prefrontal cortex activation. Rev Sci Instrum. 2009 April; 80(4):043704]. Signal processing methods, comprising not only the application of conventional linear filters to the raw EEG data, but also the nearly real-time extraction of non-linear signal features from the data, may be considered to be a part of the EEG monitoring [D. Puthankattil SUBHA, Paul K. Joseph, Rajendra Acharya U, and Choo Min Lim. EEG signal analysis: A survey. J Med Syst 34(2010):195-212]. Such features would include EEG bands (e.g., delta, theta, alpha, beta).

Detection of the phase of respiration may be performed non-invasively by adhering a thermistor or thermocouple probe to the patient's cheek so as to position the probe at the nasal orifice. Strain gauge signals from belts strapped around the chest, as well as inductive plethysmography and impedance pneumography, are also used traditionally to non-invasively generate a signal that rises and falls as a function of the phase of respiration. Respiratory phase may also be inferred from movement of the sternocleidomastoid muscle that also causes movement of the nerve stimulator during breathing, measured using accelerometers attached to the nerve stimulator, as described below. After digitizing such signals, the phase of respiration may be determined using software such as "puka", which is part of PhysioToolkit, a large published library of open source software and user manuals that are used to process and display a wide range of physiological signals [GOLDBERGER A L, Amaral L A N, Glass L, Hausdorff J M, Ivanov PCh, Mark R G, Mietus J E, Moody G B, Peng C K, Stanley H E. PhysioBank, PhysioToolkit, and PhysioNet: Components of a New Research Resource for Complex Physiologic Signals. Circulation 101 (23, 2000):e215-e220] available from PhysioNet, M.I.T. Room E25-505A, 77 Massachusetts Avenue, Cambridge, Mass. 02139]. In one embodiment of the present invention, the control unit 330 contains an analog-to-digital converter to receive such analog respiratory signals, and software for the analysis of the digitized respiratory waveform resides within the control unit 330. That software extracts turning points within the respiratory waveform, such as end-expiration and end-inspiration, and forecasts future turning points, based upon the frequency with which waveforms from previous breaths match a partial waveform for the current breath. The control unit 330 then controls the impulse generator 310, for example, to stimulate the selected nerve only during a selected phase of respiration, such as all of inspiration or only the first second of inspiration, or only the expected middle half of inspiration. In other embodiments of the invention, the physiological or environmental signals are transmitted wirelessly to the controller, as shown in FIG. 7. Some such signals may be received by the base station (e.g., ambient sound signals) and other may be received within the stimulator housing (e.g., motion signals).

Furthermore, as an option in the present invention, parameters of the stimulation may be modulated by the control unit 330 to control the impulse generator 310 in such a way as to temporally modulate stimulation by the electrodes, so as to achieve and maintain the heart rate within safe or desired limits. In that case, the parameters of the stimulation are individually raised or lowered in increments (power, frequency, etc.), and the effect as an increased, unchanged, or decreased heart rate is stored in the memory of the control unit 330. When the heart rate changes to a value outside the specified range, the control unit 330 automatically resets the parameters to values that had been recorded to produce a heart rate within that range, or if no heart rate within that range has yet been achieved, it increases or decreases parameter values in the direction that previously acquired data indicate would change the heart rate in the direction towards a heart rate in the desired range. Similarly, the arterial blood pressure is also recorded non-invasively in an embodiment of the invention, and as described above, the control unit 330 extracts the systolic, diastolic, and mean arterial blood pressure from the blood pressure waveform. The control unit 330 will then control the impulse generator 310 in such a way as to temporally modulate nerve stimulation by the electrodes, in such a way as to achieve and maintain the blood pressure within predetermined safe or desired limits, by the same method that was indicated above for the heart rate.

Let the measured output variables of the system in FIG. 11 be denoted by $y_i$ (i=1 to Q); let the desired (reference or setpoint) values of $y_i$ be denoted by $r_i$ and let the controller's input to the system consist of variables $u_j$ (j=1 to P). The objective is for a controller to select the input $u_j$ in such a way that the output variables (or a subset of them) closely follows the reference signals $r_i$, i.e., the control error $e_i=r_i-y_i$ is small, even if there is environmental input or noise to the system. Consider the error function $e_i=r_i-y_i$ to be the sensed physiological input to the controller in FIG. 11 (i.e., the reference signals are integral to the controller, which subtracts the measured system values from them to construct the control error signal). The controller will also receive a set of measured environmental signals $v_k$ (k=1 to R), which also act upon the system as shown in FIG. 11.

The functional form of the system's input u(t) is constrained to be as shown in FIGS. 2B and 2C. Ordinarily, a parameter that needs adjusting is the one associated with the amplitude of the signal shown in FIG. 2. As a first example of the use of feedback to control the system, consider the problem of adjusting the input u(t) from the nerve stimulator (i.e., output from the controller) in order to compensate for motion artifacts.

Nerve activation is generally a function of the second spatial derivative of the extracellular potential along the nerve's axon, which would be changing as the position of the stimulator varies relative to the axon [F. RATTAY. The basic mechanism for the electrical stimulation of the nervous system. Neuroscience 89 (2, 1999): 335-346]. Such motion artifact can be due to movement by the patient (e.g., head movement) or movement within the patient (e.g. sternocleidomastoid muscle contraction associated with respiration), or it can be due to movement of the stimulator relative to the body (slippage or drift). Thus, one expects that because of such undesired or unavoidable motion, there will usually be some error (e=r−y) in the intended (r) versus actual (y) nerve stimulation amplitude that needs continuous adjustment.

Accelerometers can be used to detect all these types of movement, using for example, Model LSM330DL from STMicroelectronics, 750 Canyon Dr #300 Coppell, Tex. 75019. In one embodiment, one or more accelerometer is attached to the patient's head, and one or more accelerometer is attached to the head(s) of the stimulator in the vicinity of where the stimulator contacts the patient, or an accelerometer within the smartphone is used. Because the temporally integrated outputs of the accelerometers provide a measurement of the current position of each accelerometer, the combined accelerometer outputs make it possible to measure any movement of the stimulator relative to the underlying tissue.

The location of the nerve underlying the stimulator may be determined preliminarily by placing an ultrasound probe at the location where the center of the stimulator will be placed [Michael SEIN and Imanuel Lerman. Peripheral nerve stimulator placement with ultrasound guidance for the treatment of intractable postherpetic neuralgia: A case report. Poster 267. Proceedings of the 17th Annual Meeting of the North American Neuromodulation Society. Dec. 5-8, 2013, Las Vegas, Nev., USA. page 1; SPINNER D, Kirschner J S. Accuracy of ultrasound-guided superficial trigeminal nerve blocks using methylene blue in cadavers. Pain Med 13 (11, 2012): 1469-1473]. The ultrasound probe is configured to have the same shape as the stimulator, including the attachment of one or more accelerometer. As part of the preliminary protocol, the patient with accelerometers attached is then instructed or helped to perform head movements, breathe deeply so as to contract the sternocleidomastoid muscle, and generally simulate possible motion that may accompany prolonged stimulation with the stimulator. This would include possible slippage or movement of the stimulator relative to an initial position on the patient's head. While these movements are being performed, the accelerometers are acquiring position information, and the corresponding location of the nerve is determined from the ultrasound image. With these preliminary data, it is then possible to infer the location of the nerve relative to the stimulator, given only the accelerometer data during a stimulation session, by interpolating between the previously acquired nerve position data as a function of accelerometer position data. Such data would complement imaging data that measure the extent to which the current fluorescence images of the spots on the patient's head coincide with a reference image, and therefore also measure the relative movement of the stimulator.

For any given position of the stimulator relative to the selected nerve, it is also possible to infer the amplitude of the electric field that it produces in the vicinity of the nerve. This is done by calculation or by measuring the electric field that is produced by the stimulator as a function of depth and position within a phantom that simulates the relevant bodily tissue [Francis Marion MOORE. Electrical Stimulation for pain suppression: mathematical and physical models. Thesis, School of Engineering, Cornell University, 2007; Bartosz SAWICKI, Robert Szmurlo, Przemyslaw Plonecki, Jacek Starzyński, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE '07. Amsterdam, IOS Press, 2008]. Thus, in order to compensate for movement, the controller may increase or decrease the amplitude of the output from the stimulator (u) in proportion to the inferred deviation of the amplitude of the electric field in the vicinity of the selected nerve, relative to its desired value.

For present purposes, no distinction is made between a system output variable and a variable representing the state of the system. Then, a state-space representation, or model, of the system consists of a set of first order differential equations of the form $d\ y_i/dt = F_i(t, \{y_i\}, \{u_j\}, \{v_k\};\ \{r_j\})$, where t is time and where in general, the rate of change of each variable $y_i$ is a function ($F_i$) of many other output variables as well as the input and environmental signals.

Classical control theory is concerned with situations in which the functional form of $F_i$ is as a linear combination of the state and input variables, but in which coefficients of the linear terms are not necessarily known in advance. In this linear case, the differential equations may be solved with linear transform (e.g., Laplace transform) methods, which convert the differential equations into algebraic equations for straightforward solution. Thus, for example, a single-input single-output system (dropping the subscripts on variables) may have input from a controller of the form:

$$u(t) = K_p e(t) + K_i \int_0^t e(\tau)d\tau + K_d \frac{de}{dt}$$

where the parameters for the controller are the proportional gain ($K_p$), the integral gain ($K_i$) and the derivative gain ($K_d$). This type of controller, which forms a controlling input signal with feedback using the error e=r−y, is known as a PID controller (proportional-integral-derivative). Commercial versions of PID controllers are available, and they are used in 90% of all control applications.

Optimal selection of the parameters of the controller could be through calculation, if the coefficients of the corresponding state differential equation were known in advance. However, they are ordinarily not known, so selection of the controller parameters (tuning) is accomplished by experiments in which the error e either is or is not used to form the system input (respectively, closed loop or open loop experiments). In an open loop experiment, the input is increased in a step (or random binary sequence of steps), and the system response is measured. In a closed loop experiment, the integral and derivative gains are set to zero, the proportional gain is increased until the system starts to oscillate, and the period of oscillation is measured. Depending on whether the experiment is open or closed loop, the selection of PID parameter values may then be selected according to rules that were described initially by Ziegler and Nichols. There are also many improved versions of tuning rules, including some that can be implemented automatically by the controller [L I, Y., Ang, K. H. and Chong, G. C. Y. Patents, software and hardware for PID control: an overview and analysis of the current art. IEEE Control Systems Magazine, 26 (1, 2006): 42-54; Karl Johan Åström & Richard M. Murray. Feedback Systems: An Introduction for Scientists and Engineers. Princeton N.J.: Princeton University Press, 2008; Finn HAUGEN. Tuning of PID controllers (Chapter 10) In: Basic Dynamics and Control. 2009. ISBN 978-82-91748-13-9. TechTeach, Enggravhgda 45, N-3711 Skien, Norway. http://techteach.no., pp. 129-155; Dingyu XUE, YangQuan Chen, Derek P. Atherton. PID controller design (Chapter 6), In: Linear Feedback Control: Analysis and Design with MATLAB. Society for Industrial and Applied Mathematics (SIAM).3600 Market Street, 6th Floor, Philadelphia, Pa. (2007), pp. 183-235; Jan JANTZEN, Tuning Of Fuzzy PID Controllers, Technical University of Denmark, report 98-H 871, Sep. 30, 1998].

The controller shown in FIG. 11 may also make use of feed-forward methods [Coleman BROSILOW, Babu Joseph. Feedforward Control (Chapter 9) In: Techniques of Model-Based Control. Upper Saddle River, N.J.: Prentice Hall PTR, 2002. pp, 221-240]. Thus, the controller in FIG. 9 may be a type of predictive controller, methods for which have been developed in other contexts as well, such as when a model of the system is used to calculate future outputs of the system, with the objective of choosing among possible inputs so as to optimize a criterion that is based on future values of the system's output variables.

A disclosure of the use of such feedback and feedforward methods to forecast and avert the onset of an imminent migraine attack was made in the co-pending, commonly assigned application U.S. Ser. No. 13/357,010 (publication US 2012/0185020), entitled Nerve stimulation methods for averting imminent onset or episode of a disease, to SIMON et al, which is incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A system comprising:
 an energy source that generates an electrical impulse;
 a wireless transmitter coupled to the energy source, wherein the wireless transmitter wirelessly transmits the electrical impulse and a therapy regimen;
 a mobile device that wirelessly receives the electrical impulse and the therapy regimen from the wireless transmitter;
 a stimulator coupled to the mobile device, wherein the stimulator includes a housing with a contact surface that contacts an outer skin surface of a head of a patient, wherein the stimulator transmits the electrical impulse transcutaneously through the outer skin surface to a trigeminal nerve at a target region of the head, wherein the electrical impulse modulates the trigeminal nerve such that a medical condition of the patient is treated; and
 wherein the therapy regimen includes continuously applying the electrical impulse for a time period from about 30 seconds to about 300 seconds as a single dose, wherein the therapy regimen includes applying a dose on a daily basis.

2. The system of claim 1, wherein the medical condition is at least one of a primary headache, a trigeminal neuralgia, a trigeminal neuropathy, a facial pain, or a dental pain.

3. The system of claim 1, wherein the medical condition is a primary headache.

4. The system of claim 1, wherein the electrical impulse stimulates a branch of at least one of the trigeminal nerve, a greater occipital nerve, a lesser occipital nerve, or a great auricular nerve of the patient.

5. The system of claim 4, wherein the branch of the trigeminal nerve is at least one of a supraorbital nerve, a supratrochlear nerve, an infraorbital nerve, or a mental nerve.

6. The system of claim 1, wherein the target region is restricted to a vicinity of at least one of a foramen or a notch.

7. The system of claim 1, wherein the mobile device is a mobile phone including the stimulator.

8. The system of claim 1, wherein the mobile device is a mobile phone having a surface and the stimulator attaches to the surface.

9. The system of claim 1, wherein the mobile device is a mobile wireless network device capable of receiving and transmitting data over a network.

10. The system of claim 1, further comprising:
 a signal generator coupled to the energy source, wherein the contact surface includes an electrode, wherein the signal generator generates the electrical impulse that modulates the trigeminal nerve at the target region.

11. The system of claim 10, wherein the signal generator is situated within the housing.

12. The system of claim 10, further comprising:
 a software program instructing the electrode and the signal generator to transmit the electrical impulse to the electrodes, wherein the signal generator is located exterior to the housing.

13. The system of claim 12, wherein the software program is a mobile application software program that is downloaded onto the mobile device.

14. The system of claim 10, further comprising:
 an amplifier coupled to the signal generator and the electrode, wherein the amplified amplifies the signal for the electrode.

15. The system of claim 1, further comprising:
 a base station that receives data from a remote source, wherein the base station couples to the stimulator and transmits the data to the stimulator, wherein the data includes the therapy regimen for treating the medical condition.

16. The system of claim 1, further comprising:
 a control software stored within the housing; and
 a control panel on the mobile device, wherein the control panel is coupled to the control software, wherein the control panel modulate a property of the electrical impulse.

17. The system of claim 1, wherein the electrical impulse includes bursts of pulses with each of the bursts having a frequency from about 1 burst per second to about 100 bursts per second and each of the pulses having a frequency from about 1 KHz to about 20 KHz.

18. The system of claim 1, wherein the therapy regimen includes applying 2 to 5 single doses per day.

19. A system comprising:
 an energy source that generates an electrical impulse, wherein the electrical impulse includes bursts of pulses with each of the bursts having a frequency from about 1 burst per second to about 100 bursts per second and each of the pulses having a frequency from about 1 KHz to about 20 KHz;
 a wireless transmitter coupled to the energy source, wherein the wireless transmitter wirelessly transmits the electrical impulse;
 a mobile device that wirelessly receives the electrical impulse from the wireless transmitter; and
 a stimulator coupled to the mobile device, wherein the stimulator includes a housing with a contact surface that contacts an outer skin surface of a head of a patient, wherein the stimulator transmits the electrical impulse transcutaneously through the outer skin surface to a trigeminal nerve at a target region of the head, wherein the electrical impulse modulates the trigeminal nerve such that a medical condition of the patient is treated.

20. The system of claim 19, wherein the medical condition is at least one of a primary headache, a trigeminal neuralgia, a trigeminal neuropathy, a facial pain, or a dental pain.

21. The system of claim 19, wherein the mobile device is a mobile phone including the stimulator.

22. The system of claim 19, further comprising a signal generator coupled to the energy source, wherein the contact surface includes an electrode, wherein the signal generator generates the electrical impulse that modulates the trigeminal nerve at the target region, wherein the signal generator is situated within the housing.

23. The system of claim 19, further comprising:
a control software stored within the housing; and
a control panel on the mobile device, wherein the control panel is coupled to the control software, wherein the control panel modulate a property of the electrical impulse.

24. The system of claim 19, wherein the wireless transmitter transmits a therapy regimen and the mobile device that wirelessly receives the therapy regimen from the wireless transmitter, wherein the therapy regimen includes continuously applying the electrical impulse for a time period from about 30 seconds to about 300 seconds as a single dose, wherein the therapy regimen includes applying a dose on a daily basis.

* * * * *